(12) United States Patent
Ajji et al.

(10) Patent No.: US 8,318,618 B2
(45) Date of Patent: Nov. 27, 2012

(54) NON-WOVEN MAT AND METHOD OF PRODUCING SAME

(75) Inventors: Abdellah Ajji, Mount Royal (CA); Marie Moreno, Ottawa (CA); Martin Bureau, Montreal (CA)

(73) Assignee: National Research Council of Canada, Ottawa, Ontario (CA)

( * ) Notice: Subject to any disclaimer, the term of this patent is extended or adjusted under 35 U.S.C. 154(b) by 224 days.

(21) Appl. No.: 12/452,231

(22) PCT Filed: May 21, 2008

(86) PCT No.: PCT/CA2008/000989
§ 371 (c)(1),
(2), (4) Date: Apr. 22, 2010

(87) PCT Pub. No.: WO2008/154725
PCT Pub. Date: Dec. 24, 2008

(65) Prior Publication Data
US 2010/0305687 A1  Dec. 2, 2010

Related U.S. Application Data

(60) Provisional application No. 60/929,247, filed on Jun. 19, 2007.

(51) Int. Cl.
*D04H 1/74* (2006.01)
*D04H 3/04* (2006.01)
*D04H 1/56* (2006.01)
*B32B 5/26* (2006.01)
*A61F 2/06* (2006.01)
*B27N 3/04* (2006.01)

(52) U.S. Cl. ........ 442/340; 442/366; 442/381; 442/400; 623/1.1; 623/1.44; 623/1.39; 623/1.49; 156/62.4; 156/62.8; 156/60; 156/311

(58) Field of Classification Search .......... 442/327–414; 428/105, 107, 109, 114, 119
See application file for complete search history.

(56) References Cited

U.S. PATENT DOCUMENTS

| 762,264 A | | 6/1904 | Waring | |
|---|---|---|---|---|
| 3,804,259 A | * | 4/1974 | Riggleman et al. | 210/490 |
| 3,933,557 A | * | 1/1976 | Pall | 156/167 |
| 4,323,525 A | * | 4/1982 | Bornat | 264/441 |
| 4,475,972 A | * | 10/1984 | Wong | 156/167 |

(Continued)

OTHER PUBLICATIONS

Strand definition, Textile Glossary, copyright 2001, Celanese Acetate.*

(Continued)

*Primary Examiner* — Jennifer A Steele
(74) *Attorney, Agent, or Firm* — Hans Koenig

(57) ABSTRACT

A mat having a highly uniform porosity distribution is produced by consolidating 15 or more layers of melt blown webs (or the like) having different orientations. Control over the porosity is provided by using webs that exhibit a narrow, unimodal distribution of fiber diameters over the bulk of its distribution, such as in the top 80%. A compliance of the mats can be chosen by selecting a number and orientation of the webs. It is thus possible to produce mats that are good candidates for vascular grafts, for example. The uniformity of the porosity within the range of 6 μm to 30 μm permits seeding of the vascular graft with endothelial and smooth muscle cells. The mats have the demonstrated ability to retain, and support growth of, smooth muscle cells and endothelial cells.

18 Claims, 13 Drawing Sheets

U.S. PATENT DOCUMENTS

| | | | |
|---|---|---|---|
| 5,586,997 | A | 12/1996 | Pall et al. |
| 5,653,747 | A * | 8/1997 | Dereume ..................... 623/1.54 |
| 5,891,482 | A | 4/1999 | Choi |
| 6,030,906 | A * | 2/2000 | Hassenboehler et al. ...... 442/328 |
| 6,048,808 | A | 4/2000 | Kurihara et al. |
| 6,309,423 | B2 | 10/2001 | Hayes |
| 2004/0035095 | A1 | 2/2004 | Healey |
| 2004/0054406 | A1 | 3/2004 | Dubson et al. |
| 2008/0026659 | A1 * | 1/2008 | Brandner et al. ............. 442/327 |

OTHER PUBLICATIONS

Nonwoven definition, Textile Glossary, copyright 2001, Celanese Acetate.*
Extended European Search Report dated Aug. 18, 2011 on European application 08757126.1.
Jouan, M.R., et al., "How to design a structure able to mimic the arterial wall mechanical behavior?"(2005), Journal of Materials Science 40 pp. 2675-2677.
Alimi et al., "Dilation of Woven and Knitted Aortic Prosthetic Grafts: CT Scan Evaluation", Annals of Vascular Surgery, 1994, vol. 8, p. 238-242.
Allaire et al., "The Immunogenicity of the ECM in arterial xenografts", Surgery, 1997, vol. 122, p. 73-81.
Arribas et al., "Elastic Fibres and Vascular Structure in Hypertension", Pharmacology & Therapeutics, 2006, vol. 3, p. 771-791.
Bank et al., "Direct Effects of Smooth Muscle Relaxation and Contraction on in Vivo Human Brachial Artery Elastic Properties", Web page, Circulation Research, 1995, 77:1008.
Blondel et al., "Rheological Properties of Healthy and Atherosclerotic Human Arteries", Biorheology, 2003, vol. 40, p. 369-376.
Boretos et al., "Segmented Polyurethane: A New Elastomer for Biomedical Applications", Science, 1967, vol. 158, p. 1481-1482.
Bowald et al,. "Arterial Regeneration Following Polyglactin 910 Suture Mesh Grafting", Surgery, 1979, vol. 86, p. 722-729.
Brooke et al., "Extracellular Matrix in Vascular Morphogenesis and Disease: Structure Versus Signal", Trends in Cell Biology, 2003, vol. 13(1), p. 51-56.
Chaouat et al., "The Evaluation of a Small Diameter Polysaccharide Based Arterial Graft in Rats,"Biomaterials, 2006, vol. 27, p. 5546-5553.
Chaponnier et al., "Pathological Situations Characterized by Altered Actin Isoform Expression", The Journal of Pathology, 2004, vol. 204(4), p. 386-395.
Courtman et al., "The Role of Crosslinking in Modification of the Immune Response Elicited Against Xenogenic Vascular . . . ", J. Biomed. Mater. Res., 2001, vol. 55, p. 576-586.
Deng et al., "Calcitonin Gene-Related Peptide and Hypertension", Peptides, 2005, vol. 26(9), p. 1676-1685.
Donaldson et al., "Femoral-distal bypass with in situ greater saphenous vein", Ann. Surg., 1991, vol. 213, p. 457-465.
Edelman ER, "Vascular Tissue Engineering: Designer Arteries", Circ. Res., 1999, vol. 85, p. 1115-1117.
Faury et al., "Function-structure relationship of elastic arteries in evolution: from microfibrils to elastin and elastic fibres", Pathol. Biol., 2001, vol. 49, p. 310-325.
Friedman et al., "Biomaterials: an historical perspective", Implantation Biology: the Host Response and Biomedical Devices, 1994, p. 1-12.
Friedman et al., "A prospective randomized comparison of Dacron and polytetrafluoroethylene aortic bifurcation grafts", Surgery, 1995, vol. 117, p. 7-10.
Gozna et al., "Necessity for elastic properties in synthetic arterial grafts", Can. J. Surg., 1974, vol. 17, p. 176-179.
Green et al., "Prosthetic above-knee femoropopliteal bypass grafting: five-year results of a randomized trial", J. Vasc. Surg., 2000, vol. 31, p. 417-425.
Greenwald et al., "Improving vascular grafts: the importance of mechanical and haemodynamic properties", J. Pathol., 2000, vol. 190, p. 292-299.
Greisler et al., "Partially bioresorbable vascular grafts in dogs", Surgery, 1991, vol. 110, p. 645-655.

Higgins et al., "Effects of polyglycolic acid on porcine smooth muscle cell growth and differentiation", J. Biomed. Mater. Res., 2003, vol. 67A, p. 295-302.
Hirai et al., "Highly oriented, tubular hybrid vascular tissue for a low pressure circulatory system", ASAIO J., 1994, vol. 40, p. M383-338.
Hirai et al., "Venous reconstruction using hybrid vascular tissue composed of vascular cells and collagen: tissue regeneration . . . ", Cell Transplant., 1996, vol. 5, p. 93-105.
Hoerstrup et al., "Living, autologous pulmonary artery conduits tissue engineered from human umbilical cord cells", Ann. Thorac. Surg., 2002, vol. 74, p. 46-52.
Hoerstrup et al., "Tissue engineering of small caliber vascular grafts", Eur. J. Cardiothorac. Surg., 2001, vol. 20, p. 164-169.
Holthofer et al., "Ulex europaeus I lectin as a marker for vascular endothelium..", Laboratory Investigation; A Journal of Technical Methods.., 1982, vol. 74(1), p. 60-66.
Hormia et al., "Factor VIII-related Antigen. A pericellular matrix component of cultured human endothelial cells", Exp. Cell Research, 1983, vol. 149(2), p. 483-497.
Jouan et al., "How to design a structure able to mimic the arterial wall mechanical behaviour?", Journal of Materials Science, 2005, vol. 40, p. 2675-2677.
Kakisis et al., "Artificial blood vessel: The Holy Grail of peripheral vascular surgery", J. Vasc. Surg., 2005, vol. 41, p. 349-354.
Laurent et al., "Elastic modulus of the radial artery wall material is not increased in patients . . . ", Arterioscler Thromb. Vasc. Biol., 1994, vol. 14(7), p. 1223-1231.
Learoyd et al., "Alterations with age in the viscoelastic properties of human arterial walls", Circ. Res., 1966, vol. 18, p. 278-292.
L'Heureux et al., "A completely biological tissue-engineered human blood vessel", FASEB J., 1998, vol. 12, p. 47-56.
L'Heureux et al., "In vitro construction of a human blood vessel from cultured vascular cells: a morphologic study", J. Vasc. Surg., 1993, vol. 17, p. 499-509.
Marois et al., "Vascugraft polyurethane arterial prosthesis as femoropopliteal and femoro-peroneal bypasses in humans..", Biomaterials, 1996, vol. 17, p. 1289-1300.
Matthews et al., "Smooth muscle cell migration in electrospun poly(lactic acid) and collagen/elastin", Cardiovasc. Pathol., 2002, vol. 11, p. 13.
Moreno et al., "Calcitonin gene-related peptide (CGRP)", Encyclopedia of Endocrine Diseases, 2004, vol. 1, p. 425-435.
Moreno et al., "Efficacy of the non-peptide CGRP receptor antagonist BIBN4096BS . . . ", Neuropharmacology, 2002, vol. 42, p. 568-576.
Moreno et al., "New fibrous PET structures for vascular grafts: effects of fiber structure on endothelial . . . ", Vascular Matrix Biology and Bioeng. Workshop, Whistler 2007.
Nerem RM, "Tissue engineering a blood vesel, regulation of vascular biology by mechanical stresses", Biochem., 1994, vol. 56, p. 204-209.
Nicol et al., "Cell adhesion and growth on synthetic elastomeric matrices containing arg-gly-asp-ser", J. Biomed. Mater. Res., 1992, vol. 26, p. 393-413.
Niklason et al., "Functional arteries grown in vitro", Science, 1999, vol. 284, p. 489-493.
Nunn et al., "Postoperative dilation of knitted Dacron aortic bifurcation graft", J. Vasc. Surg., 1990, vol. 12, p. 291-297.
Prager et al., "Collagen versus gelatin coated Dacron versus stretch polytetrafluoroethylene in abdominal aortic bifurcation graft . . . ", Surgery, 2001, vol. 130, p. 408-414.
Santerre et al., "Biodegradation evaluation of polyether and polyester-urethanes with oxidative and hydrolytic enzymes", J. Biomed. Mater. Res., 1994, vol. 28, p. 1187-1199.
Scott et al., "A collagen coated vacular prosthesis", J. Cardiovasc. Surg. (Torino), 1987, vol. 28, p. 498-504.
Seliktar et al., "Dynamic mechanical conditioning of collagen-gel blood vessel constructs induces remodeling in vitro", Ann. Biomed. Eng., 2000, vol. 28, p. 351-362.
Shinoka et al., "Creation of viable pulmonary artery autografts through tissue engineering", J. Thorac. Cardiovasc. Surg., 1998, vol. 115, p. 536-546.

Shum-Tim et al., "Tissue engineering of autologous aorta using a new biodegradable polymer", Ann. Thorac. Surg., 1999, vol. 69, p. 2298-2305.

Simmonds et al., "Designing nonwovens to meet pore size specifications", J. of Engineered Fibers and Fabrics, 2007, vol. 2(1), p. 1-15.

Sreerekha et al., "Cultivation of endothelial progenitor cells on fibrin matrix and layering . . . ", Artifical Organs, 2006, vol. 30(4), p. 242-249.

Stanimirovic et al., "Angiotensin II-induced fluid phase endocytosis in human cerebromicrovascular endothelial cells . . . ", J. Cell Physiol., 1996, vol. 169, p. 455-467.

Taylor et al., "Present status of reversed vein bypass grafting: five-year results of a modern series", J. Vasc. Surg., 1990, vol. 10, p. 220-225.

Teebken et al., "Tissue engineering of vascular grafts: human cell seeding..", Eur. J. Vasc. Surg., 2000, vol. 19, p. 381-386.

Teebken et al., "Cell seeded decellularised allogenic matrix grafts and biodegradable polydioxanone-prostheses . . . ", Eur. J. Vasc. Surg., 2001, vol. 22, p. 139-145.

Toshiharu et al., "Midterm clinical result of tissue-engineered vascular autografts seeded with autologous . . . ", J. Thorac. Cardiovasc. Surg., 2005, vol. 129, p. 1330-1338.

Urry et al., "Elastic protein-based materials in tissue reconstruction", Ann. N.Y. Acad. Sci., 1997, vol. 831, p. 32-46.

Weinberg et al., "A blood vessel model constructed from collagen and cultured vascular cells", Science, 1986, vol. 231, p. 397-400.

Wilson et al., "Acellular matrix allograft small caliber vascular prostheses", ASAIO Trans., 1990, vol. 36, p. M340-M343.

Wilson et al., "Acellular matrix: a biomaterials approach for coronary artery bypass and heart valve replacement", Ann. Thorac. Surg., 1995, vol. 60(2 suppl), p. S353-S358.

Xue et al., "Biomaterials in the development and future of vascular grafts", J. Vasc. Surg., 2003, vol. 37, p. 472-480.

Zhang et al., "Vascugraft polyurethane arterial prosthesis as femoropopliteal and femoro-peroneal bypasses in humans..", Biomaterials, 1997, vol. 18, p. 113-124.

Ziegler et al., "Tissue engineering a blood vessel, regulation of vascular biology by mechanical stresses", J. Cell Biochem., 1994, vol. 56, p. 204-209.

* cited by examiner

PPH441-8Kg/h 120°C [0/90]₁₀

PPH441-8Kg/h 150°C [0/90]₁₀

PPH441-8Kg/h 150°C [0/90]

PPH441-8Kg/h 150°C [0/90/0]

NON-WOVEN MAT AND METHOD OF PRODUCING SAME

CROSS-REFERENCE TO RELATED APPLICATIONS

This application is a national entry of PCT/CA2008/000989 filed May 21, 2008, which claims the benefit of U.S. Provisional Patent Application Ser. No. 60/929,247 filed Jun. 19, 2007, which is herein incorporated by reference in its entirety.

FIELD OF THE INVENTION

The invention relates in general to non-woven mats and to a novel method of producing same, and, in particular, relates to a non-woven mat formed by pressing a plurality of differently oriented web sections of a web produced, for example, by extrusion fiber melt blowing. The mats have a uniformity of porosity and a compliance that makes it acceptable, for example, for application as a vascular graft.

BACKGROUND OF THE INVENTION

It is known in the art to produce felts by applying pressure and heat to a tangle of threads. It has also long been known to produce multi-ply felt by pressing bats of fleeces together, for example bats of differing quality as taught by U.S. Pat. No. 762,264 to Waring.

At least since the early 1990s thin webs of synthetic fibers have been produced by a technique known as extrusion fiber melt blowing. The process basically involves extruding multiple strands through a line of holes in a fiber melt blowing die, and allowing the parallel strands to tangle while molten, to provide cohesion between the strands when cooled, forming the web.

Extrusion fiber melt blowing produces molten strands having a distribution of thicknesses that become randomly tangled. As the strands are contact welded at tangle contact points, the resulting web generally has lower strength in one direction, i.e. the direction orthogonal to the direction of extrusion. There are many applications of melt blown webs that are applied to backings or other layers formed differently.

U.S. Pat. No. 6,048,808 to Kurihara et al. teaches a non-woven fabric of stretched filaments of polymers of different kinds, having a strength equal to that of a woven fabric, and a method for manufacturing the same. The fabric is characterized in that the nonwoven fabric is provided with stretched filament webs comprising long filaments formed out of a plural kinds of thermoplastic polymers of different properties, the long filaments as a whole being aligned in one direction. The fabric may be composed of threads that are spun-bonded or melt-blown. Kurihara et al. teach that a nonwoven fabric can be obtained by laminating webs of different aligned directions. Both crosswise and obliquely intersecting ways are applicable to laminating either longitudinally aligned webs or transversely aligned webs. Kurihara et al. require webs of different kinds of polymers be used, as does lamination, the method of binding the webs, and the product resulting from the teachings of Kuirhara et al. does not have the useful properties described in the present invention.

U.S. Pat. No. 5,891,482 teaches a melt blowing apparatus for producing a layered filter media web product. A die apparatus wherein a layered web of melt blown fibrous filter media is produced by a unitary die including several die sources with facing layers of the fibrous filter media being attenuated by opposed fluid streams at preselected included angles and with the fiber layers being free from bonding together and with the fibers in each layer being minimally bonded.

United States patent application publication number 2004/0035095 to Healey teaches a non-woven filter composite and a method for forming the composite. According to Healey, a cost effective, high efficiency, low pressure drop, adsorptive, non-woven filter media is provided comprising a high surface area synthetic microfiber, e.g., melt blown, fine fiber layer. The filter media can also include one or more non-woven spun bond layers and can be combined with a coarse fiber support layer. The coarse fiber support layer can itself be a low pressure drop synthetic microfiber, e.g., melt blown, layer adhered to a spunbond layer, and can serve as a prefilter to enhance overall performance.

Accordingly, it is known to produce a composite having a plurality of different non-woven layers.

Furthermore as taught in *Journal of Materials Science* 40 (2005) 2675-2677 entitled "How to design a structure able to mimic the arterial wall mechanical behavior" to Jouan et al., it is known to produce non-woven mats of polypropylene fibers (6-14 µm in diameter), by applying a heat treatment (15 min. at 120-150° C.) to a stack of 20 melt blown webs. Stress-strain curves of the mats produced by different temperatures of the heat treatment were compared with that of a femoral artery.

There remains a need for a non-woven mat that is inexpensive to produce, and has useful mechanical properties, including a uniform porosity.

SUMMARY OF THE INVENTION

Applicant has discovered that by subjecting a stack of differently oriented melt blown webs, or the like, to pressure and heat, a resulting mat can be produced. The mat will have desirable properties, such as a uniform porosity, that is, a porosity having a narrow average size distribution, if the fibers of the mats are of a controlled distribution. Specifically if at least a bottom 80% of the fiber diameter distribution is substantially a normal distribution (i.e. has a regression coefficient (R) greater than 0.95, more preferably greater than 0.96, and more preferably greater than 0.97), and the standard deviation and/or range of the bottom 80% of the fiber diameter distribution is relatively small, and at least 15 webs are used, a highly uniform porosity distribution results. For example, the standard deviation may be less than 2 µm, more preferably less than 1.75 µm, more preferably less than 1.5 µm, more preferably less than 1.4 µm, and/or the range may be less than 5 µm, more preferably less than 4 µm, and more preferably less than 3 µm, and more preferably less than 2.5 µm. If a desired pore size distribution is uniform and centered between 5 to 20 µm, a mean fiber diameter of the bottom 80% of the fibers between about 1.5 and 5.5 µm, more preferably 1.75 and 4.5 µm, and more preferably 2 and 4.5 µm, is useful.

As melt blown webs are relatively inexpensive to manufacture, the consolidation of these webs to produce mats having desirable properties constitutes a highly cost-effective technique for producing mats.

The mat may have 15 or more layers, 16 or more layers, 18 or more layers, 20 or more layer, 22 or more layers, 25 or more layers or 30 or more layers. The mat may have less than 50 layers, or less than 40 layers or less than 35 layers.

The webs may have surface densities of 0.1-10 g/m², or from 0.5-5 g/m², or from 1-3 g/m².

The differences in orientations of two or more layers may be from about 3° to 90°, from about 5° to 90°, from about 10° to about 90°, or from about 15° to about 90°.

The strand diameters of the mats may have average diameters ranging from 200 nm to 300 μm, and has a chosen fiber diameter distribution. Generally the presence of 5-20% of fibers having strand diameters above (and possibly significantly above) the narrow distribution that accounts for the vast majority of the fibers is not expected to significantly alter the porosity either in terms of amount of porosity, or its size distribution. The lower bulk of the strand distribution (lower 80% for example) that includes the finest and the vast majority of the strands should represent a more relevant property for determining the porosity attributes. The strand diameter distributions of the most uniform porosity mats produced are also marked as having substantially unimodal, and relatively smooth distributions, for at least the bottom 80% of the strand diameters.

For cellular growth, a number of pores above the size of the cell should be limited and a high porosity is required to permit fluid transport between the cells. For example, cells which have 10-20 μm diameters in a smallest direction (e.g. smooth muscle cells and endothelial cells) will require substantial porosity of the substrate, but will have to provide pores small enough so that the cells can be supported. Given this constraint, it is desirable to have less than 20%, more preferably less than 15% and more preferably less than 10% of the fiber diameters above 20 μm, and at least 40%, more preferably at least 45% of the fiber diameters below 10 μm. This has been accomplished by controlling the mean of the bottom 80% of the fibers to lie between about 1 and about 8 μm, more preferably between 2 and 6.5 μm, and more preferably between 4 and 5 μm. For example, if a porosity of about 10 μm is desired, a center diameter of around 3 or 4 μm (ranges of 2-6 μm, 2-4 μm) have been found useful.

Applicant has further discovered that a method of producing a mat having a high porosity of considerably uniform distribution is provided by pressing many webs. Uniformity of the porosity is achieved after a critical number of webs are applied. The specific number will vary with the properties of the webs (polymer, density, fiber diameter distribution, degree of orientation, etc.), but if polyethylene terephthalate (PET) is used to produce the webs, and the webs have substantially all (80%) fibers with diameters between 2-7 μm, and web densities of about 2.0 g/m$^2$, the number of webs is greater than about 16, and a uniform distribution of pores ranging from 1-20 μm in diameter are provided. By choosing a number of webs above 16, and by selection of the orientations of the webs, a compliance (in given directions) and other parameters of the mat can be tailored to particular applications. The same web-forming process (extrusion melt blown) can be used to generate PET webs having fiber diameters as low as 200 nm, and accordingly a variety of other ranges of porosities can be provided using this forming method.

Applicant has further discovered that mats produced with 15 or more such webs have a uniformity of porosity as well as a compliance that make them good candidates for vascular grafts. The uniformity of the mean pore diameter within the range of 6 to 20 μm facilitates ingrowth of cells including endothelial and smooth muscle cells desired for a vascular graft. Advantageously, the cells can be seeded prior to implantation.

Using the uniform porosity mat, Applicant has found that cell ingrowth can be provided without the coating of the mat with extracellular matrix proteins such as gelatin. Furthermore human brain endothelial cells (HBEC) and smooth muscle cells (SMC) grown in the uncoated uniform porosity mats retain their specific phenotype, the ability to produce extracellular matrix proteins, such as collagen and elastin, and maintain calcitonin-gene related peptide (CGRP) receptor expression and adenilate cyclase machinery for vasodilatation, suggesting that the application of the mats as grafts will not impair, but will facilitate continued vasodilatation within the grafted region of a blood vessel. Furthermore, both sides of a mat of the present invention can be independently seeded with respective cells.

Conditions of the stacking of the webs may be chosen to select a preferred density of contact fused points, and a strength of the bonding of the contact points.

Accordingly a method of producing a mat is provided, the method begins with producing a web of a tangle of strands of a polycondensation polymer contact fused at tangle points. The strands have substantially a same mean orientation defining an orientation of the web, and the strands have a diameter distribution such that at least a bottom 80% of the diameters are substantially unimodal and have a standard deviation of less than 2 μm. More preferably the at least the bottom 80% of strand diameters have a standard deviation of less than 1.75 μm, and a regression coefficient measure of fit to a normal distribution of at least 0.96. At least 15 sections of these webs are laid in a stack so that the orientations of at least two web sections are substantially different, and then heat and pressure are applied to the stack of webs to produce the mat, the heat being at a temperature above a glass transition temperature and below a melting point of the polymer. The use of the same web to form the stack has numerous advantages for cost effective production. As the same web will have similar properties in terms of sheet density, and mean fiber distribution, it will provide uniform densities within the mat. Herein sections of a web refers to parts of one or more web made from the same polymer using substantially the same web-forming apparatus and parameters.

The polycondensation polymer is preferably not highly hydrophobic, and may be, for example, a polyester or a polycarbonate, for example. More specifically it may be one of: polyethylene terephthalate (PET), polycarbonate (PC), polytrimethylene terephthalate (PTT), and polylactic acid (PLLA), or combinations thereof. Most preferably PET, PTT, or PLLA is used.

The stacking of the webs, and distribution of the fiber diameters, are chosen to produce a desired pore size distribution. The pore size distribution may be strongly peaked, for example with 80% or 90% of the pores having a range of 10 μm. A pore size distribution having 90% of the pores having an average equivalent diameter less than 20 μm has been found beneficial for supporting cellular cultures.

Stacking the webs may involve applying groups of same orientation web sections above and below differently oriented web sections, and may involve substantially alternating orientations of groups of web sections. The webs may be stacked on a mold.

A mat of uniform porosity may be achieved by stacking at least 15 webs.

Producing the web may involve extruding and stretching the strands, preferably using extrusion fiber melt blowing one or more webs and cutting the one or more webs to form the plurality of webs. The extrusion fiber melt blowing may involve subjecting a molten tangled strand output to a roller for providing a desired degree of orientation of the molten tangled strands.

A mat is also provided, the mat being formed from a plurality of oriented web sections of a same web stacked and compressed together, wherein the web is formed of substantially oriented, extruded strands of a polycondensation polymer that is not highly hydrophobic, the strands are contact-fused at tangle points, at least a bottom 80% of the strand diameters are substantially unimodal and have a standard deviation with 2 μm and the orientations of at least two of the web sections are substantially different.

The mat may be formed as a cylindrical or planar mat.

Accordingly there is also provided a vascular graft formed from a cylindrical mat and having a compliance close to that of a blood vessel. The vascular graft may have a luminal inner wall seeded with endothelial cells, and/or an abluminal outer wall seeded with smooth muscle cells. The elastic modulus of the mat is comparable to that of a blood vessel.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

The invention provides a mat formed from a plurality of oriented webs stacked and pressed together, where each web is formed of substantially oriented strands, that are tangled and contact-fused at tangle points, such as the output of an extrusion fiber melt blowing apparatus. The orientations of at least two adjacent webs are significantly different, and the webs are composed of a same material.

Figure 1:
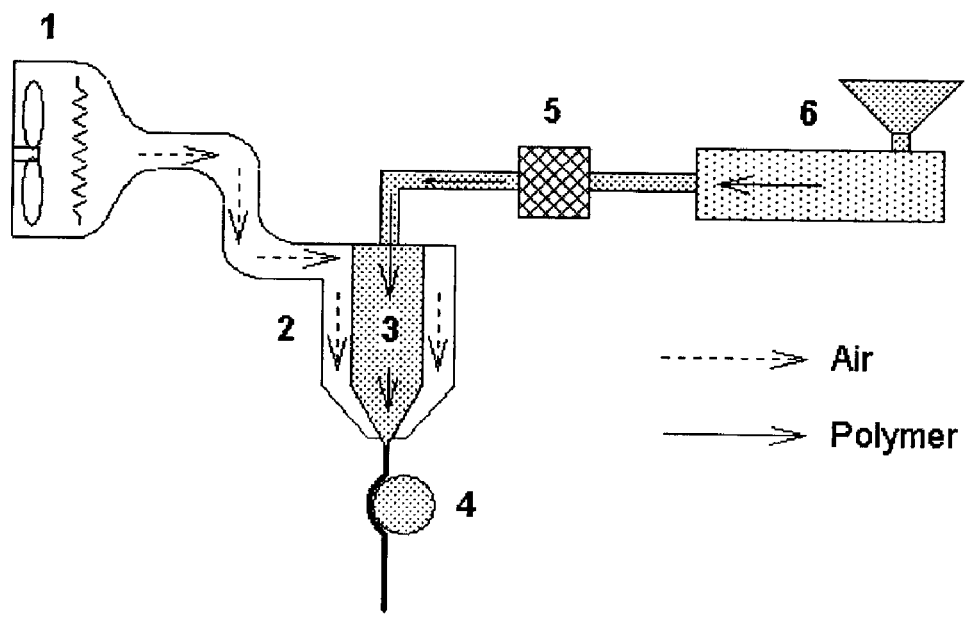
FIG. 1 is a schematic illustration of an extrusion fiber melt blowing apparatus.

FIG. 1 schematically illustrates an extrusion fiber melt blowing apparatus. The blow melt extruder provides two channels, one for molten polymer, and the other for heated air, which meet at a point of extrusion.

The extrusion fiber melt blowing apparatus shown has forced heated air supply 1 in fluid communication with a manifold 2 which surrounds a die 3, although this is not required. Basically an equal pressure on opposite sides is generally desired to reduce a likelihood of shearing the molten strands. The heated air supply provides the air at a flow rate that is chosen to stretch the strands a desired amount less than a breaking point of the extruded strands, and at a temperature range that depends on a polymer extruded.

In accordance with the apparatus used by the Applicant in the examples below, the heated air can be varied from about 280° C. to about 320° C., resulting in a desired thickness and strength of the strands produced. Naturally the thickness and strength also depends on a draw rate of the extruder, and dimensions of the die, as will be understood by those of skill in the art. The heated air serves to draw the fibers stretch them, and keep them in the molten state. It will be appreciated that different polymers may require more rapid cooling in order to provide contact fusing at tangle points and accordingly the heated air supply may be significantly cooler or, in some embodiments, may be ambient or even chilled air. Furthermore fluids other than air could be used to increase or decrease the draw pressure on the exiting strands as may be required for different polymers, or different dimensions of melt blow die apertures. The die 3 has an egress directly above a driven roller 4.

A polymer material is fed into a hopper 6 where it is melted. Molten polymer is fed to the die 3 at a flow rate that is controlled and stabilized by a gear pump 5, which maintains a substantially constant fluid pressure of the polymer melt within the die 3.

The egress of the die 3, i.e. die tip 7 has a linear array of holes through which individual strands of the polymer melt are extruded, and vents for directing the heated air onto the exiting strands, as is known in the art. For example, dies are known having 200 to 400 apertures of diameters ranging from 200 to 400 μm, and separations around 500 μm, with lengths of about 6-8 inches.

The passive roller 4 is positioned vertically and horizontally, and driven to achieve desired degrees of tangling and orientation within the web produced. Because of the heated air, the strands exiting the die remain partially molten during contact with the roller 4. Accordingly, upon tangling, the tangle points are contact-fused and subsequent cooling results in the formation of a web. The roller 4 is positioned to meet the strands a distance below the apertures, the distance being chosen so that the polymer is cooled sufficiently before meeting the roller so that the molten strands do not puddle or pool on the roller, but not so cool as to have completely solidified, in which case little or no contact-fusing will occur at tangle points (i.e. points at which tangled strands touch). Naturally this distance depends on a temperature of the molten polymer, a rate of extrusion, a temperature and volume of the hot air, thermal interaction of the air and molten strand, ambient temperature, thickness of the strands, etc.

A horizontal position of the roller determines an angle that the strands meet the roller. This angle can vary between 0° and 180°. The horizontal position and the rate of revolution of roller, and strand extrusion rate determine a dwell time of the strands on the roller, and a tension applied to the strands (apart from the pressure applied by the air supply). The roller may be driven at different rates from 100 to 1000 rpm and changing this rate within limits of stresses that can be applied to the cooling strands, has an impact on the degree to which the strands are tangled, and the degree to which they are oriented. Generally the slower the rotation, the less stress is applied to the strands by the roller, resulting in less elongation of the strands, and the longer the strands dwell on the roller. The longer the dwell time the more tangled the strands become, resulting in higher sheet/surface densities of the web.

Figure 2A:
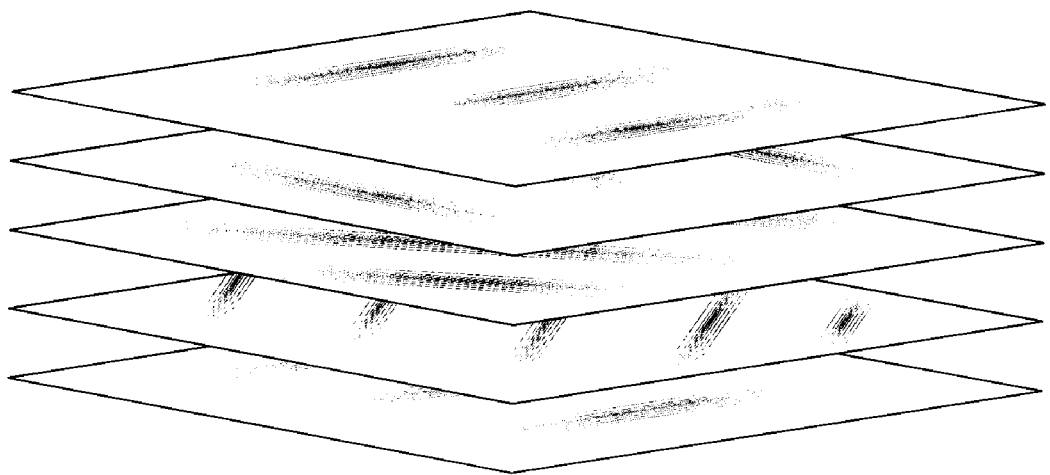
FIGS. 2a,b are schematic illustrations of stacks of webs for producing planar and cylindrical webs respectively.
Figure 2B:
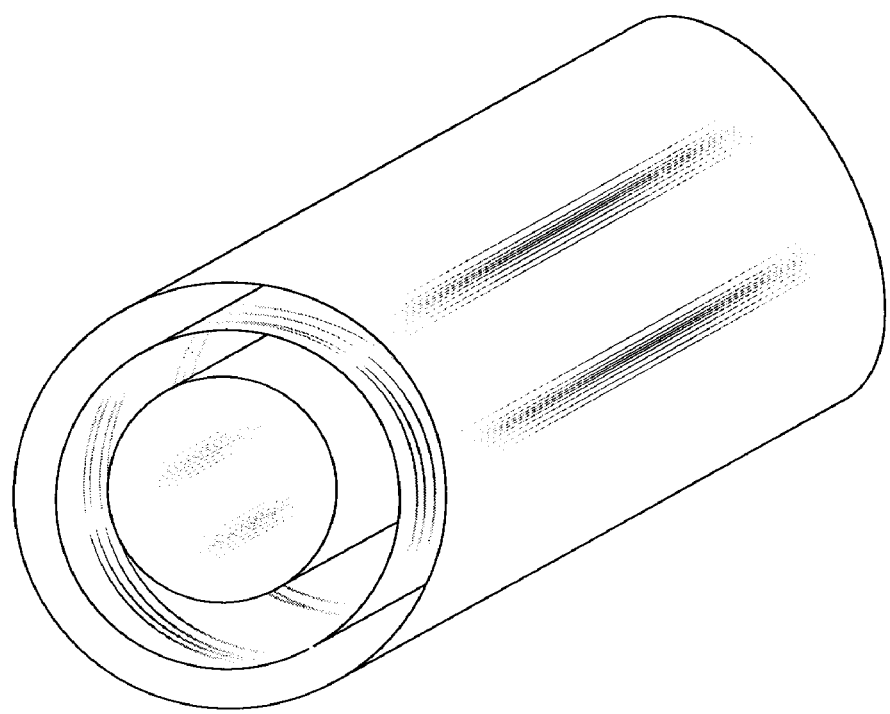

FIGS. 2a and b schematically illustrate a planar stack and a cylindrical stack of a few plies of the web. Each ply of the web is oriented at a substantially different angle from the previous ply, and the angles between orientations of the first and subsequent webs vary from 0° to 90°. It will be appreciated that these webs can be stacked and/or cut by any applicable mechanical process.

Figure 3:
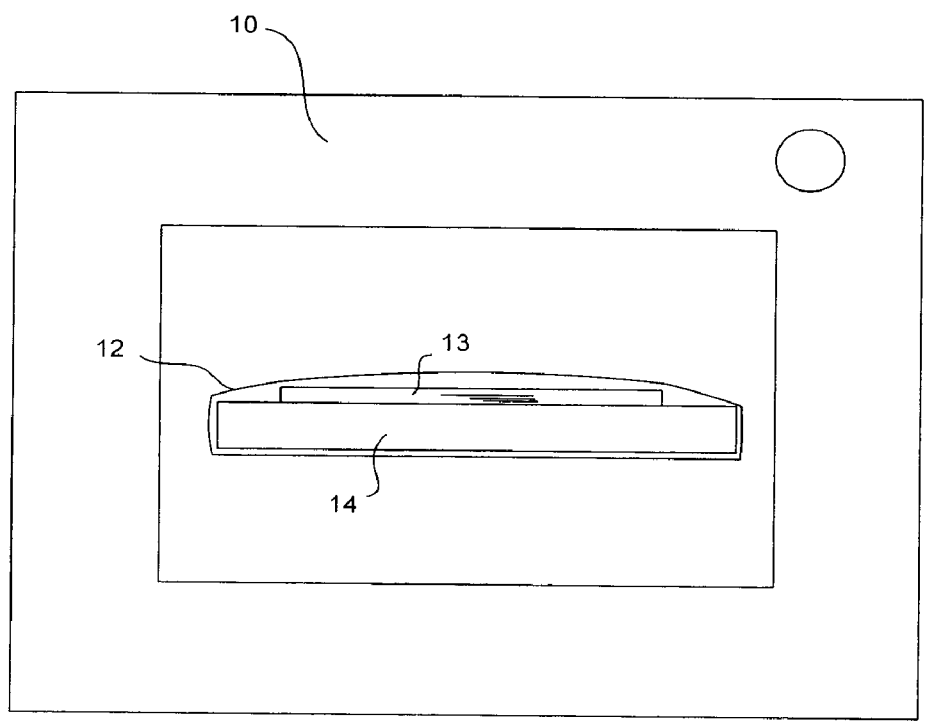
FIG. 3 is a schematic illustration of an apparatus for mat forming.
Figure 4A:
FIGS. 4a-e are microscope images of five mats M1 . . . M5 having different webs and/or different numbers of webs.
Figure 4B:
Figure 4C:
Figure 4D:
Figure 4E:
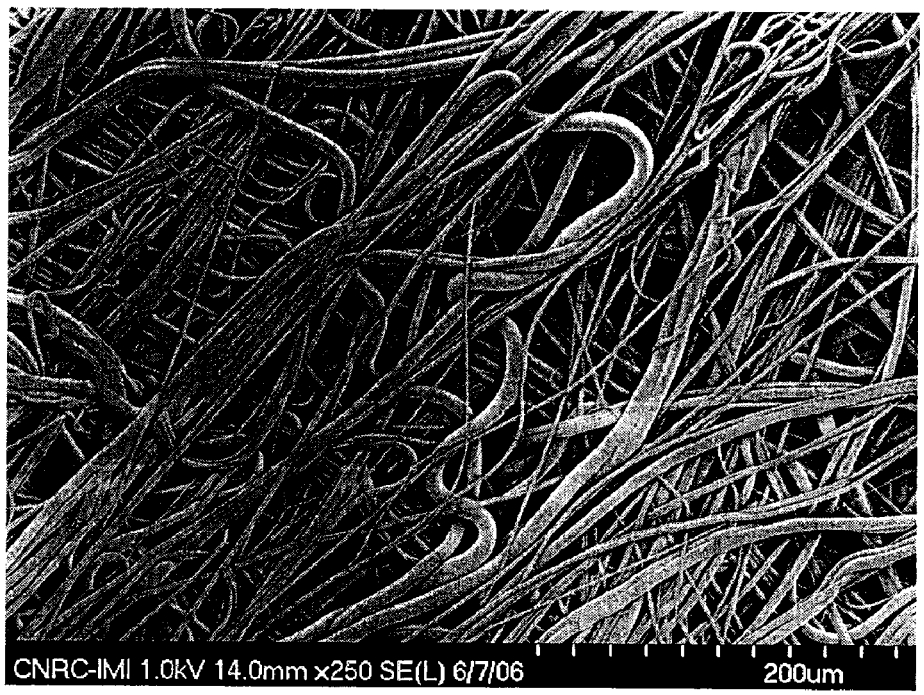

FIG. 3 schematically illustrates a mat forming apparatus for applying heat and pressure to a stack of webs. FIG. 3 shows an oven 10 containing a sealed evacuated bag 12 containing the stack of webs 13 held against a support structure 14. The evacuation of the air within the bag causes a continuous pressure to be applied across the surface of the stack, pressing the stack against the support structure. The temperature is in a range between a glass transition temperature and a melting point of the polymer, the temperature being closer to the melting point, the more crystalline the polymer is.

Alternatively the web forming can be performed in an autoclave, as well known in the art. Autoclaves are designed to apply a wide range of pressures and temperatures to a stack of webs for forming a mat. The pressure and temperature required to consolidate the webs to a desired degree naturally depends on the nature of the webs (density and fiber diameter), and the nature of the polymer used.

Example 1

Materials

Polyethylene terephthalate (PET) was to produce non-woven webs in accordance with these examples. The grade of PET used, Selar-pt 7086 supplied by Dupont, has an inherent viscosity of 1, and was pretreated by drying at 120° C. for at least 4 hours.

It will be appreciated by those of skill in the art that other melt extruded webs can be formed using polycarbonate (PC), or polyesters, such as polytrimethylene terephthalate (PTT), and polylactic acid (PLLA) among others. Applicant has also produced extrusion fiber melt blown webs with polypropylene (PP). Specifically, the PP Valtec HH441 having a melt flow rate of 400 g/10 min and supplied by ExxonMobil was used.

It is known that the principles of melt blowing can be applied to produce webs of other polymers if the thermal, and thermo-mechanical properties of the polymer melt are matched with the die, thermodynamic regime of the die and a correct fluid stream is used to draw/blow the strands from the die.

Method of Web Formation

Webs (or veils) of non-woven fibers (i.e. strands) were produced using a fiber melt blowing process. Three batches of webs were formed from PET using slightly different processes: W1, W2, and W3.

The PET was introduced as pellets and melted at 312° C. A flow rate was established by control of a gear pump, which fed a die having a blow melt tip. The air was heated to 320° C. and a fan cycling at 1,000 RPM was used to force the heated air through the manifold surrounding the die, and out through vents adjacent line of holes in the die. The extruded strands were directed onto a roller driven at 200 rpm. The roller was 20 cm below the die tip, and met the roller (smooth steel cylindrical roller) at an angle of about 90°.

The die contained 230 aligned holes (about 300 μm in diameter). Air was blown through a narrow gap 2 mm wide extending parallel to the line of holes of the die. The air allowed for stretching of the fibers as well as assisting in the drawing of the strands through the holes. Applicant has achieved strand thicknesses varying from 200 nanometers minimum diameter to 300 μm by changing the flow rate of the molten polymer (from 12 kg/hr-0.5 kg/h) and the fan rate between 500 rpm and 1300 rpm. Examples of batch W1, W2 and W3 webs were produced with strand diameters having the distribution shown in FIG. 6.

W1 webs were produced as follows: the PET flow rate was 2.05 kg/hr with a PET melt pressure of 225 Psi; the air temperature was 320° C., the fan was driven at 1000 rpm; and the roller was driven at 200 rpm.

W2 webs were produced using the same apparatus, but were extruded at a higher rate (the PET flow rate was 2.4 kg/hr with a melt pressure of 260 psi), and the fan was driven at 500 rpm. The roller was again driven at 200 rpm.

For W3 webs, the flow rate was 1.25 kg/hr, and the melt pressure 125 psi. The air temperature was again 320° C., and the fan cycled at 1000 rpm. The roller rotated at 105 rpm.

The same apparatus can be used to produce webs from PP, but used different parameters. The flow rate of polymer was in the range of 4-12 kg/hr, fan rate between 800 and 1300 rpm, the PP melt temperature was in the range of 260-300° C. Furthermore the rolls were driven between 300 and 800 rpm. Only ambient air was used for blowing the strands.

As the strand diameters of the webs are not expected to change significantly during the mat forming, the distributions of diameters of the strands of these webs can be determined from images of FIGS. 4a-e, where 4a-c are all produced from W1 webs having a density of 1.955 $g/m^2$, 4d is produced from W2 webs having a density of 1.731 $g/m^2$, and 4e is produced from W3 webs having a density of 1.924 $g/m^2$. It will be noted that in all mats except M4 at least 75% of the fibers have diameters ranging over less than 5 μm.

Methods of Mat Forming

First Example

Both planar mats and cylindrical mats were prepared for mechanical testing. The planar mats were produced by stacking various numbers of individual webs onto a planar aluminum plaque. The webs were stacked by hand under minimal tension and trimmed to produce coupons of a size 20 cm×20 cm for planar mats. The mat thickness depended on the number of webs stacked and was about 100 μm for 20 layers. The plaques were then placed in pressurized bags and, by evacuating the air in the bags, an even vacuum pressure was applied to the coupons. The vacuum bag was placed in an oven at 90° C. for 30 minutes.

Second Example

Cylindrical mats, of about 30 cm in length, were produced on a 6-mm diameter mandrel from 20 W1 webs with alternating orientations. Each web was laid on the mandrel and cut so that edges of the web substantially abutted each other defining a seam. The seams of adjacent webs were not aligned to prevent a weakness from being defined throughout the cylindrical stacks. The mandrel was then inserted into an autoclave for 30 minutes exposing the cylindrical stacks to 90° C. and a pressure of 50 psi for 30 minutes.

Third Example

A third example of mat forming involved applying a slightly different pressure and temperature regime, and was found to provide better bonding. The temperature was marginally raised to 100° C., for a slightly shorter duration of 20 minutes, with under vacuum conditions (i.e. the mat is subjected to a pressure of about 14.7 psi).

These forming conditions were applied to produce cylindrical mats. Pressure was applied using a vacuum bag method which substantially reduced the defects caused by the wrinkling of the bag along the two opposite sides of the bag where the inner surface of the bag meets itself to form a seam. As will be appreciated, the pressure applied to the mat along this seam is less, and there is a tendency for the pressure to nip the material rather than press it toward the mandrel. The pressure along the seam was significantly improved by surrounding the mat with a thermoplastic film, which served as a bleeding layer for the compression, improving the uniformity of the pressure applied to the mandrel.

Other methods and systems for applying pressure and heat in a controlled manner could equally be used to consolidate the webs to produce such cylindrical mats.

Properties of Mats

Five kinds of planar mats were produced using webs of batch W1, W2 and W3: namely, mats M1 . . . M5 (please note these are respectively referred to as structures A . . . E in the figures). Mats M1 . . . M3 were made from W1 webs, and differ only in the number of webs in the stacks used to produce them. M1 mats were formed of 10 W1 webs, mats M2 were formed of 15 W1 webs, and mats M3 were formed of 20 W1 webs. In each of these examples, the webs were oriented and adjacent webs were stacked with orthogonal orientations. Mats M4 and M5 were stacks of 20 layers of W2 and W3 webs, respectively.

Figure 5:
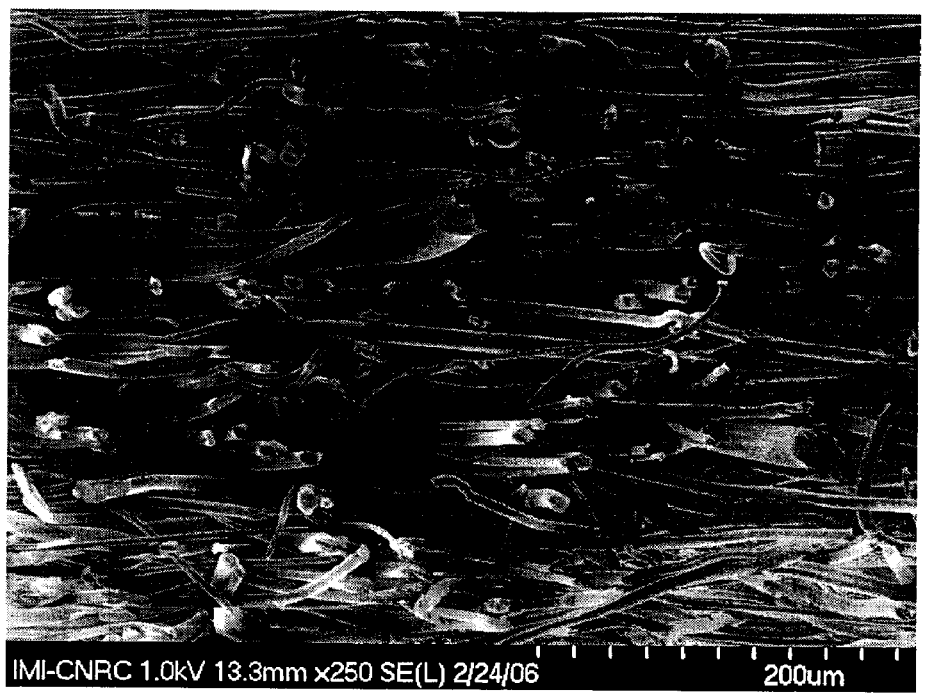
FIG. 5 is an image of a typical cross-section micrograph of a mat.

Plane micrographs of the five mats are presented in FIGS. 4a-e. A micrograph of a sectioned representative sample is shown in FIG. 5. While the illustrations are particularly of the mats produced using the first mat forming method, images of the mats made by the second and third mat forming methods are equally well represented by the images of FIGS. 4b,c, and e, which are similar.

Figure 6:
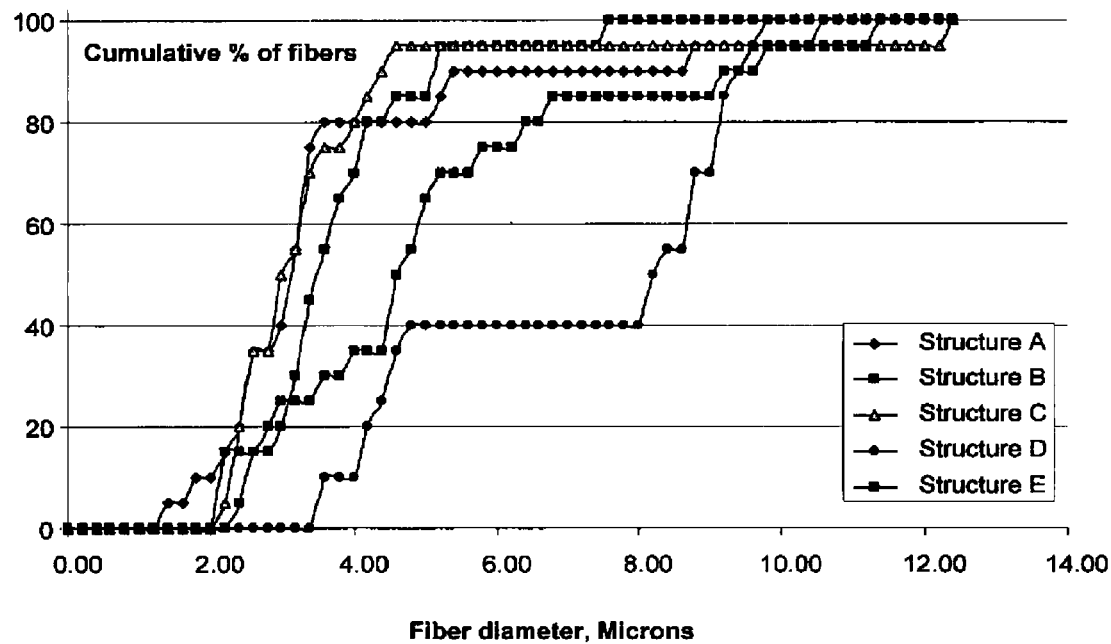
FIG. 6 is a graph showing fiber size distribution, in terms of cumulative percent of fibers as a function of diameter for mats M1 . . . M5.

FIG. 6 shows a cumulative percent of fibers as a function of fiber diameter. It can be clearly seen that the mats M1 . . . M3 have about the same distribution (substantially within experimental errors). The fiber diameters of M1 . . . M3 are mostly between less than 1 and about 4 µm (more than 80% of the fibers, the next 10% are between 4 and 5.5 µm, and the last 10% being between about 8-12 µm.

The mats having a second most uniform fiber diameter distribution are M5 (80% of the fibers are between 2 and 6.5 µm, the rest ranging from 6.5 to less than 10 µm).

The widest distribution of fiber diameters is present in mat D: between 4 and 10 µm. In fact two populations are present in mat D: 40% between 3 and 5 µm and 60% between 8 and 10 µm.

The measurements of fiber thicknesses were computed by image analysis on 3 images from the plane of mats and 3 from the cross-section images of the mats. About 50 measurements were made for fibers diameter distributions and 150 for pore size distributions (see FIG. 8).

Mats produced using the third method of web forming were experimentally indistinguishable on these measures.

Mechanical Testing on Planar Mats

A variety of mechanical characteristics were obtained for planar mats made by stacking W1 batch webs with various stacking patterns. The stacking pattern is identified as follows: $[0°_a/90°_b]_c$-denotes a pattern that consists of a number (a) of W1 webs all oriented in parallel (at an angle of 0° with an axis) on top of which are b W1 webs, all of which are oriented at an angle of 90° (although another angle could be used) to axis, if a and/or b are absent, it refers to a single web; and the number (c) that follows indicates a number of repetitions of the pattern were stacked. An angle following the stack constitution indicates an angle at which the mechanical testing was performed, relative to the axis. The characteristics are summarized in the Table 1:

TABLE 1

Compliances of Mats M1 . . . M5

| | Young's modulus (MPa) | Yield stress (MPa) | Deformation at Yield (%) | Deformation at rupture (%) |
|---|---|---|---|---|
| $[0°/90°]10$-$0°$ | 252 ± 62 | 6.4 ± 1.0 | 5.5 ± 1.1 | 38 ± 12 |
| $[0°_2/90°_2]5$-$45°$ | 180 ± 15 | 4.1 ± 0.4 | 4.4 ± 0.4 | 40 ± 6 |
| $[0°_5/90°_5]2$-$45°$ | 171 ± 17 | 3.9 ± 0.3 | 4.3 ± 0.3 | 32 ± 4 |
| $[0°_{10}/90°_{10}]1$-$45°$ | 158 ± 20 | 3.5 ± 0.5 | 3.7 ± 0.3 | 21 ± 2 |

The tests were performed in tension mode using an Instron micromechanical tester (Instron 5548) directly on coupons cut from the mats. Testing was done at room temperature at a crosshead speed of 10 mm/min according to testing conditions recommended in ASTM D638. Pneumatic grips with rubber faces were used to hold and pull the specimen tested. Values of Young's modulus, yield stress and deformation at yield and deformation at rupture were obtained respectively from the initial linear region, from deflection point at the end of first linear region towards a flattened regime, and from final load decay on the load-extension slope.

It will be noted that a variety of compliance values can be obtained by varying a number of layers and the orientations.

Mechanical Testing on Cylindrical Mats

Example 1

Compliance measurements on about 15 cylindrical mats made according to the second mat forming method (using 20 W1 webs) were performed on a custom-made test apparatus. This test apparatus consists of a rod-mounted balloon connected to a pressurized nitrogen line via a pressure regulator. The cylindrical mats were inserted onto the rod-mounted balloon. Both applied pressure and the cylindrical mat diameter upon stretching were measured and logged. The pressure was monitored through a pressure transducer (AP-34K, Keyence Canada Inc.). The cylindrical mat diameter was measured using a laser scanner (LS-3100, Keyence Canada Inc.). The cylindrical mats tested were 5 cm in length and 6.35 mm in diameter (unstretched).

The cylindrical mats were submitted to 100 pressure cycles between 0 and 200 mmHg. Pressure was applied to the cylindrical mats at an approximate rate of 200 mmHg per sec. Pressure-diameter measurements were collected at a rate of 10 points per sec. Measurements of compliance, C, were made from the pressure-diameter curves according to Equation 1:

$$C = \frac{\Delta D}{D_o \cdot \Delta P} \quad (1)$$

where $\Delta D$ refers the variation of diameter when a variation of pressure $\Delta P$ is applied to a cylindrical mat with an initial diameter $D_o$. The incremental modulus of elasticity, $E_{inc}$, of the mats is calculated in a first approximation as its initial modulus of elasticity, given by Equation 2 [29]:

$$E_{inc} = \frac{D_o}{2 \cdot h \cdot C} \quad (2)$$

where h is the thickness of the cylindrical mat. Assumptions were made that the mat was uniform and cylindrical, and that it could be considered as an incompressible elastic thin wall tube.

Figure 7A:
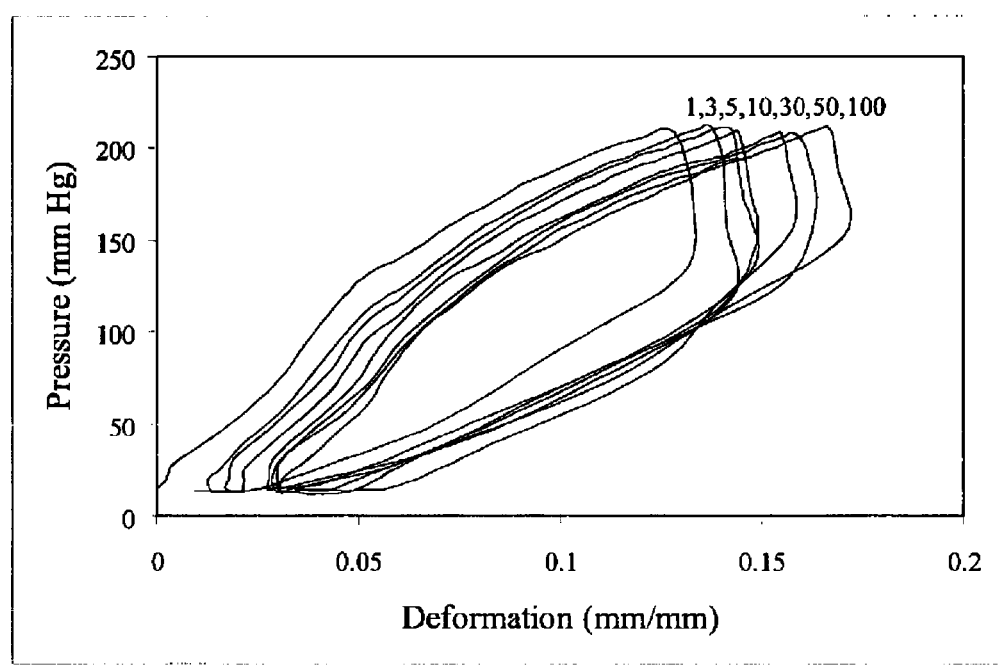
FIGS. 7 a,b are graphs showing pressure-deformation curves resulting from cyclic pressure testing on cylindrical mats M5.

The modulus of the cylindrical mat was measured using our custom-made set-up. Pressure-diameter curves are shown in FIG. 7a for cycles 1, 3, 5, 10, 30, 50, and 100. These curves show that the cylindrical mat exhibits an approximately constant compliance (initial slope) and that it undergoes a slight permanent deformation (e.g., 0.05 mm/mm) upon pressure cycling, when passing from cycle 1 to 100. It will be noted that the meaningful parts of the curve are the initial slope (after the initial tension is applied to the cylindrical mat, until the pressure reaches its maximum), and that the remainder of the curves are schematic.

The average modulus obtained from Equation 2 for the 100 cycles is 1.0±0.05 MPa.

Example 2

In an attempt to improve on the above experiment, the balloon was replaced with a balloon that had a more uniform opening mechanism that didn't present an artifact during the low pressure phase of the testing. The former balloon had a collapsing structure having folds running spirally around the balloon, and therefore twisted during an initial part of inflation.

The second example uses a cylindrical mat made with the third mat forming method. The rest of the experimental details are the same as that of the first radial testing example.

Figure 7B:
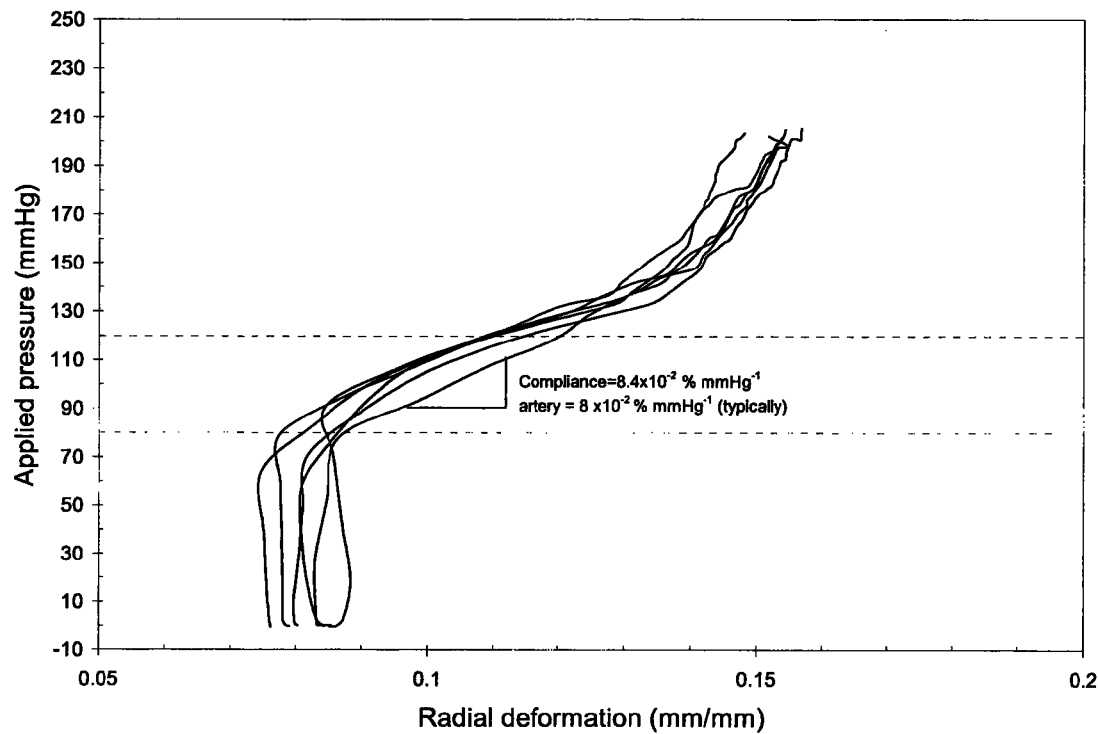

FIG. 7b is a graph of pressure deformation curves during the increasing pressure phases of cycles 1, 5, 10, 30, 50, and 100, showing the meaningful parts of the curve. In comparison with the graph of FIG. 7a, it will be noted that the stability of the mat throughout the cycling, which is inversely proportional to the displacement of the curves (in the x direction) between the first and last cycles, is significantly improved. Specifically that about one fifth the displacement of the mats consolidated as per the second forming method will be noted. At the same time it is noted that the width of the curve was lower indicating a stronger cohesion of the material and a smaller deformation in response to an equal stress. Furthermore the linearity of the stress-strain curve is better, showing that the artifact attributed to the unfolding of the balloon in the earlier example is removed.

The average compliance calculated from Equation 1 for the 100 cycles is 8.4±1.0×10$^{-2}$%/mmHg and the average calculated modulus for the 100 cycles is 1.7±0.2 MPa.

Burst Pressure Testing on Cylindrical Mats

The cylindrical mats made with the third mat forming method were first subjected to the 100 repeated inflating cycles to produce the pressure deformation curves, and then was subjected to an applied pressure of 200 mmHg continuously for 10 minutes without any additional changes in diameter (i.e any additional radial deformation) related to creep of the structure. Then the pressure was increased until the structure failed, which is called the burst pressure. The burst pressure was 1325 mmHg.

Example 2

Porosity

Figure 8:
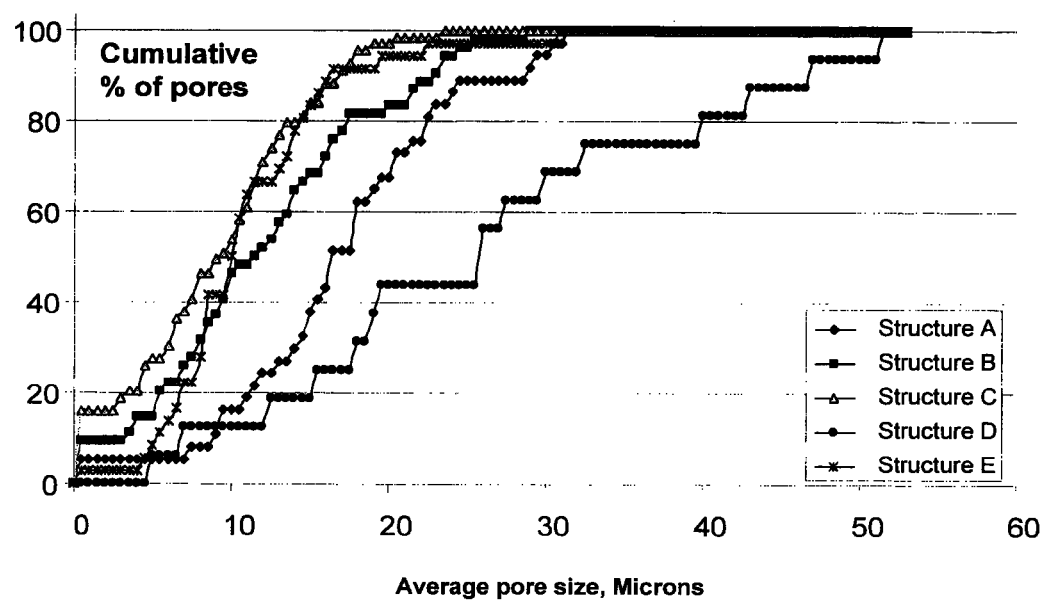
FIG. 8 is a graph showing pore size distribution, in terms of cumulative pore size percent as a function of average equivalent diameter of pores for mats M1 . . . M5.
Figure 9A:
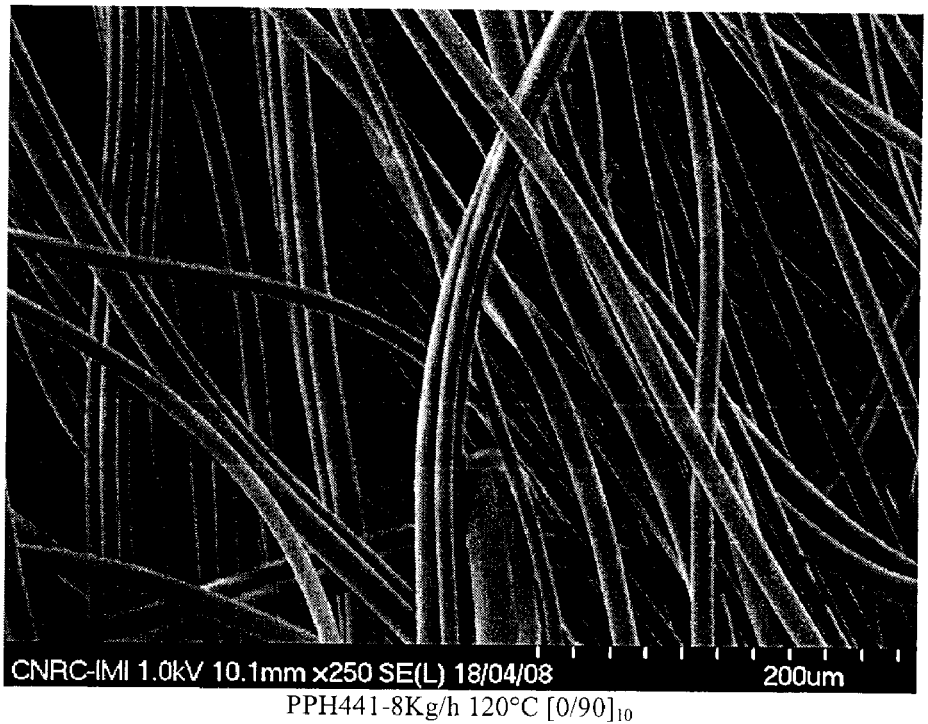
FIG. 9 a-e are microscope images of five mats made of PP.
Figure 9B:
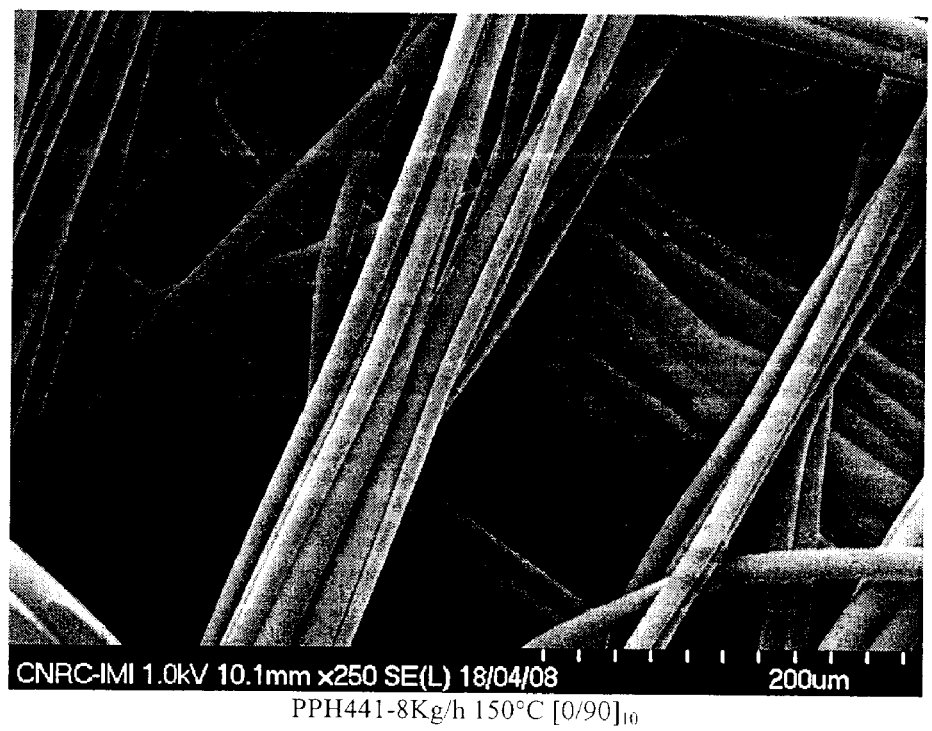
Figure 9C:
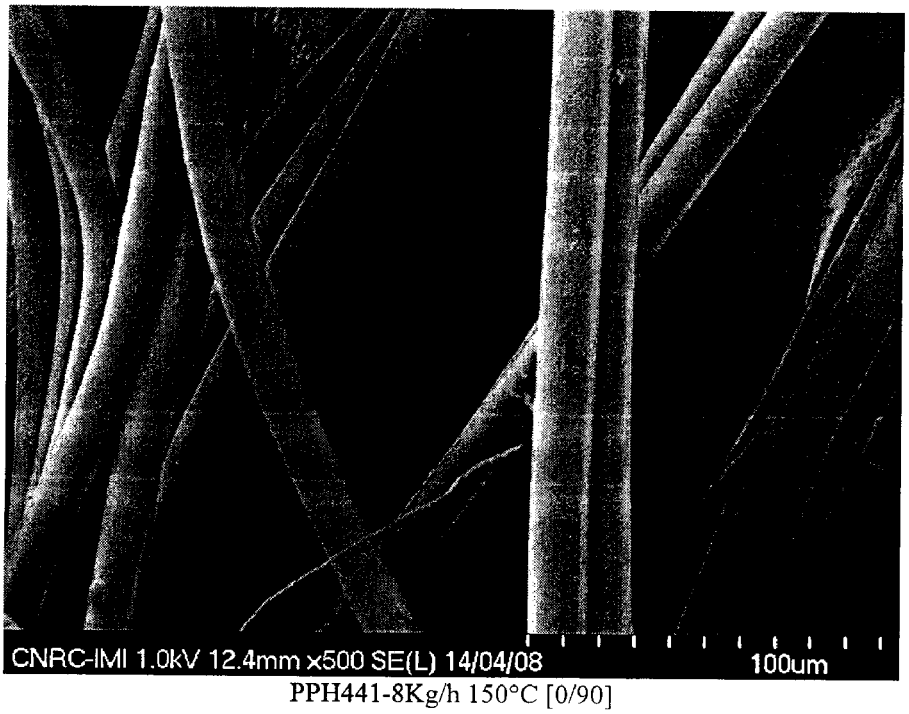
Figure 9D:
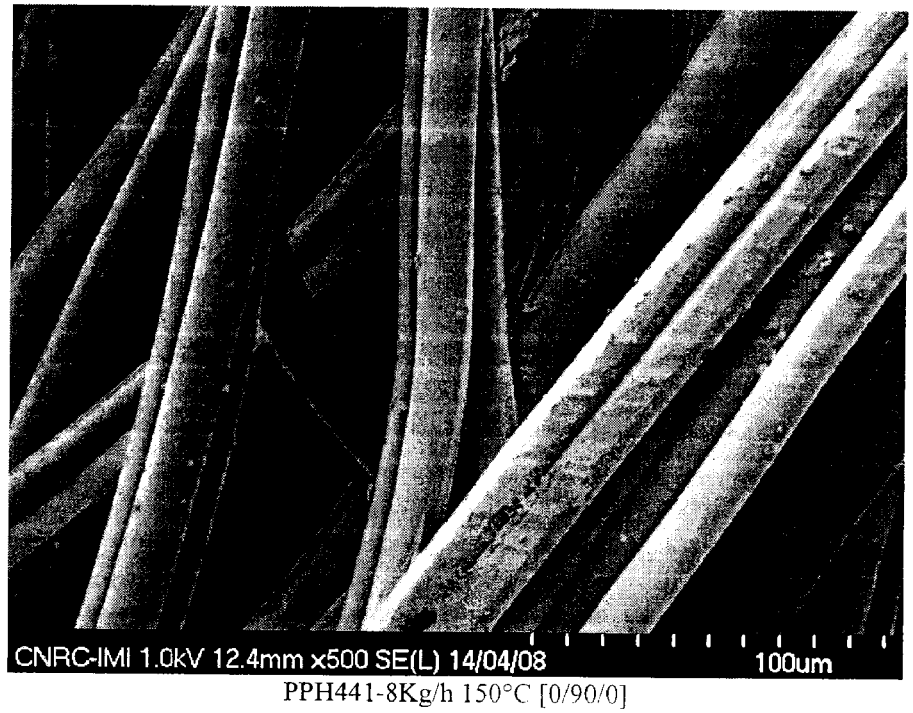
Figure 9E:
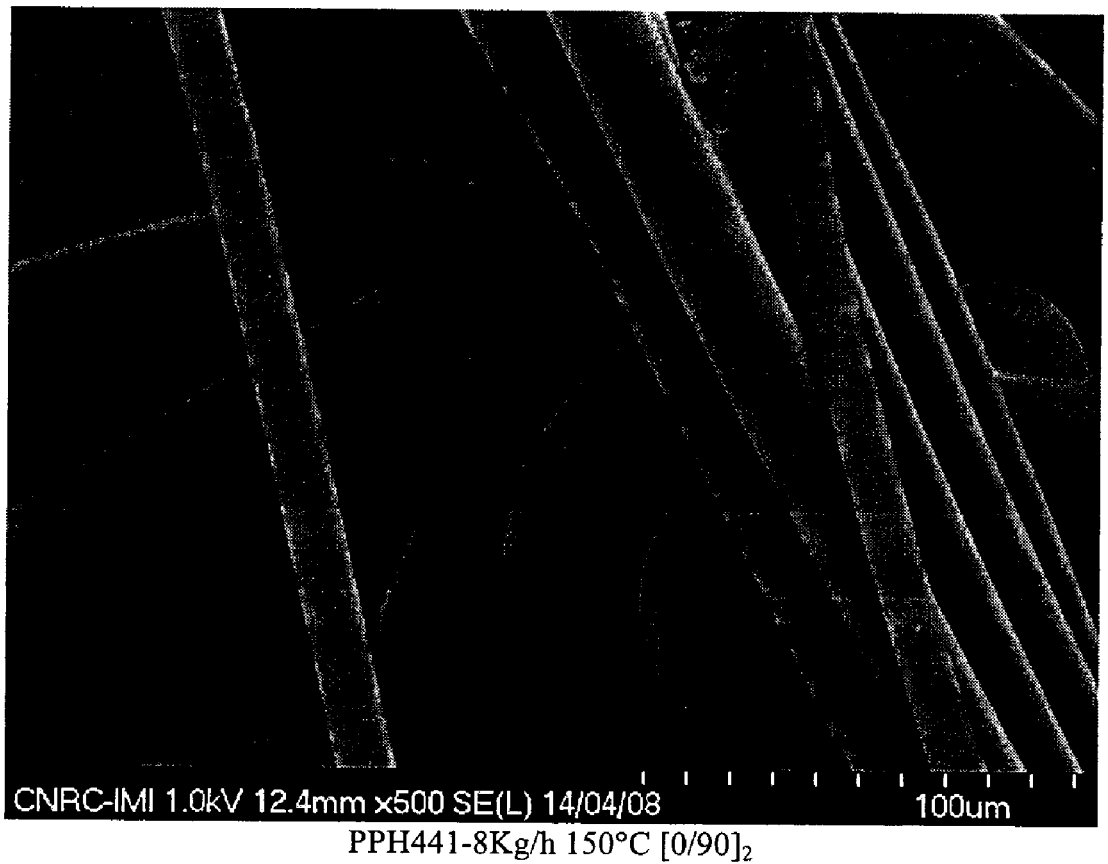

The mats M1 . . . M5 are examined to determine a porosity distribution on the surface and throughout the mat. FIG. 8 is a graphical representation of results of porosity measurements performed on each of mats. FIG. 8 plots the cumulative percent of pores as a function of their average equivalent diameter. The average equivalent diameter is a diameter of a circle having the same area as the pore at the intersection of a plane.

Mats M1 . . . M3 differ in the number of fiber stacks, which is expected to have an effect on average pore size. This is clearly shown in FIGS. 4a-c: mat M1 (which has the least number of stacks) shows a distribution of pore size between 8 µm and 30 µm, mat M2: between 3 µm and 27 µm and mat M3: between 1 µm and 20 µm. The tightest distribution among these 3 mats is thus mat M3. Mat M5 has a close distribution of pore size to mat M3, minor differences are observed at the low end of the distribution, whereas mat M4 shows a large distribution of pore sizes with large pores (up to 50 µm).

It is noted that about 90% of the pores have a dimension less than 20 µm in M3 and M5, and that at least 50% of the pores have a dimension between 5 and 17 µm. It will be noted that less than 20%, even less than 15% and even less than 10% of the pores measured have pore sizes above 20 µm, and further that more than 40%, and even more than 45% of the pore have sizes below 10 µm.

The narrow dimensional distribution of pores and the high porosity of these mats are features that make them potentially very useful for many applications. For example, a uniformity of pore size may be useful for certain filters, such as air filters, or for keeping particles of a given size in relative isolation from each other. About 90% of the pores have diameters from 0-17 µm, and 80% are from 0-14 µm.

Prior Art Comparative Example

Mats of PP

As taught by *Journal of Materials Science* 40 (2005) 2675-2677 to Jouan et al. referred to above, mats of PP were produced by stacking 20 plies and applying a mat forming treatment comprising exposing the mats to temperatures of 120, 130, 140 and 150° C. It is not clear having regard to the paper, whether all the mats have a same orientation or whether the orientations alternate by 90° each time. Having regard to the reported 3-layer example having 50% orientation of fibers it would be reasonable to conclude that the 50% orientation must be an intrinsic property of the webs. Applicant has now obtained the specific webs used and found that they are substantially oriented, and concludes that what must have been intended in the paper is that the webs were oriented with alternating layers orthogonal. Applicant concludes that the 3 layer data examples were interpolated based on samples having an even number of layers. The paper indicates that these webs can be used to produce mats by changing orientations of the webs with respect to each other, to increase a compliance of the mats, to improve a match with that of a vascular wall.

The webs/veils used to prepare mats like those characterized by Jouan et al. were produced using polypropylene homopolymer (PPH, Valtec HH441 having a melt index of 400 g/10 min and supplied by ExxonMobil) extruded at a rate of 8 Kg/h. It is widely known that PPH is very hydrophobic. This presents numerous difficulties for many applications, and would be expected to severely limit adhesion with cells, and cell growth.

Applicant has reproduced the mats described in Jouan et al. using the following conditions. Four stacks of different numbers of webs of alternating orthogonal orientations were laid: 20 [0°,90°]10, 2 [0°,90°], 3 [0°,90°,0°] and 4 [0°,90°]2. Mats of each of these 4 thicknesses were formed using a 0.5 mm thick frame-type mold placed in a Carver press (type F21123 model #M) under a pressure of 30 psi.

The extremes of the temperature conditions in the prior art paper (i.e. 120° C. and 150° C.) were used to represent the variety of mats produced according to Jouan et al. In each pressing application, the pressure was applied for 10 minutes after the temperature was obtained to reproduce the results faithfully.

Table 2 schematically illustrates the average, maximum, minimum, and median fiber diameters within the resultant mats, as computed from images presented as FIGS. 9a-e, as well as the standard deviation of diameter. It will be appreciated that the means of strand diameter of each sample is nominally the same, in that 14.9 µm is within the standard deviation of each measure.

TABLE 2

Fiber distribution for 8 PRIOR ART PP examples

| Fiber (µm) | 120° C. [0/90]$_{10}$ | 150° C. [0/90]$_{10}$ | 120° C. [0/90]$_1$ | 150° C. [0/90]$_1$ | 120° C. [0/90/0]$_1$ | 150° C. [0/90/0]$_1$ | 120° C. [0/90]$_2$ | 150° C. [0/90]$_2$ |
|---|---|---|---|---|---|---|---|---|
| ave | 15.2 | 15.1 | 15.1 | 14.3 | 13.7 | 16.1 | 13.6 | 16.2 |
| max | 18.6 | 22.7 | 18.7 | 16.9 | 20.5 | 21.2 | 23.1 | 24.4 |
| min | 10.1 | 10.5 | 11.5 | 11.2 | 10.7 | 11.4 | 8.6 | 9.4 |
| stdev | 2.9 | 3.7 | 2.2 | 2.0 | 3.4 | 3.2 | 4.3 | 4.4 |
| med | 15.7 | 13.7 | 14.2 | 14.9 | 12.6 | 15.1 | 12.4 | 14.8 |

The diameters of the fibers of which the mats are composed, have a distribution between about 10 to about 20 µm. Jouan et al. asserts that the fiber diameters were 6-14 µm. By either account this distribution is significantly broader (8-10) than the examples (mats M2, M3, and M5), if you remove the top 20% of the distribution. Specifically the range is 8-10 µm, and the standard deviation is over 2 µm.

Table 3 lists the computed average, maximum, minimum and median pore diameter of the two 20 ply mats. Naturally the porosities of the mats having 4 or fewer webs were incomparable.

TABLE 3

Porosity distribution of PRIOR ART PP examples

| Pore diameter | average | maximum | minimum | std deviation | median |
|---|---|---|---|---|---|
| 120° C. [0°/90°]10 | 42.1 | 109.5 | 8.2 | 19.6 | 36.6 |
| 150° C. [0°/90°]10 | 54.6 | 127.4 | 11.2 | 25.1 | 50.0 |

It will be noted that this pore distribution is broader than that defined by (mats M2, M3, and M5). Pores ranging from 10 to 100 µm have limited applications as depending on the pore size, different retention, flow and other parameters are produced. Accordingly these examples do not demonstrate the advantages that can be achieved for producing a narrow porosity distribution, even if it had been produced of a polymer suitable for cell growth.

Without being limited to the foregoing theory in all aspects of the invention, Applicant posits that the narrow distribution of porosity achieved in the invention is the result of a narrow, unimodal distribution of the bottom 80% of the fiber diameters. Table 4 lists statistical properties of the five mats M1 . . . M5 and the two examples of PP mats formed at 120 and 150° C., respectively. The distributions are for the entire range of fiber distributions.

TABLE 4

Fiber distributions comparison over entire distribution

| Fiber(µm) | M2 | M3 | M5 | M4 | PP120 | PP150 |
|---|---|---|---|---|---|---|
| Min | 2.33 | 2.16 | 2 | 3.43 | 10.14 | 10.51 |
| Max | 7.48 | 12.21 | 11.3 | 9.72 | 18.58 | 22.72 |
| Mean | 3.7735 | 3.5475 | 5.095 | 6.9855 | 15.192 | 15.146 |
| Median | 3.545 | 3.055 | 4.7 | 8.19 | 15.74 | 13.73 |
| Std Dev | 1.1557 | 2.1576 | 2.5496 | 2.4325 | 2.8583 | 3.6814 |

It will be noted that the distributions on the left (which produced narrow porosity distributions) and those on the right (which did not produce narrow porosity distributions) are not very dissimilar.

TABLE 5

Fiber distributions comparison over bottom 80% of distribution

| Fiber(µm) | M2 | M3 | M5 | M4 | PP120 | PP150 |
|---|---|---|---|---|---|---|
| Average | 3.3356 | 2.8631 | 4.0625 | 5.9807 | 14.594 | 13.715 |
| Minimum | 2.3300 | 2.1600 | 2.0000 | 3.4300 | 10.140 | 10.51 |
| Maximum | 4.1900 | 3.8700 | 6.4000 | 8.7800 | 17.900 | 17.67 |
| Median | 3.3050 | 2.9100 | 4.5000 | 4.6050 | 15.730 | 13.41 |
| Std Dev | 0.55804 | 0.52147 | 1.3495 | 2.2363 | 2.6906 | 2.1345 |

Note that the bulk of the fibers in mats the left hand side have the bottom 80% fiber distribution with a standard deviation less than 2, and even less than 1.4 µm. On the right hand side the fiber distributions are considerably over 2 µm.

A general difference is also noted between the profiles of the fiber diameter distributions of the right hand examples and left hand examples, in terms of how uniform they are. The fiber diameter distributions were subjected to standard regression analysis, to measure the fit of these values to a normal distribution centered on the average. The standard regression coefficients (R) are listed in the table below, indicate a measure of fit of the data points to the normal distribution centered on the respective median, are as follows:

TABLE 5

Unimodality of fiber distributions

| Fiber(μm) | M2 | M3 | M5 | M4 | PP120 | PP150 |
|---|---|---|---|---|---|---|
| R 100% | 0.71753 | 0.90277 | 0.94901 | 0.90277 | 0.95441 | 0.95674 |
| R 80% | 0.9878 | 0.97524 | 0.97229 | 0.89752 | 0.95104 | 0.98378 |

It is noted that the bulk (bottom 80%) in the left examples are highly unimodal (i.e. R>~96). M4, the PET mat that is more similar to M2, M3 and M5 is significantly bimodal. PP 120 does not significantly change its regression coefficient depending on inclusion or exclusion of the top 20%.

Example 3

Graft Application

It is noted that the average compliance and incremental modulus of elasticity of the cylindrical mats produced for mechanical testing compare well with reported $E_{inc}$ values for external iliac (Blondel 2000), carotid and abdominal (Learoyd 1966), radial wrist (Laurent 1994) and brachial (Bank 1995) arteries, which vary between 1 and 5 MPa. This demonstrates that it is possible to reproduce the compliance of arteries with nonwoven fiber mats. This compliance figure differs significantly from the reported Dacron modulus values and expanded polytetrafluoroethylene (ePTFE) shown in Table 6.

TABLE 6

Elastic modulus of graft polymers

| Materials | Elastic modulus (based on compliance) |
|---|---|
| Arteries* | 1 to 5 MPa |
| Dacron (woven structure) | 2000 to 4000 MPa |
| ePTFE (porous membrane) | 400-1800 MPa |
| This work (avg. of 100 pressure cycles) | 1.0 ± 0.05 MPa |

The compliance matching of the graft with that of an artery, for example, permits the graft to be implanted and would not require replacement at the rate of current grafts (such as Dacron and ePTFE), which may be formed of the same polymers, but are not as compliant, resulting in thrombogenicity.

For cellular growth, a number of pores above the size of the cell should be limited. For example, cells which have 10-20 μm diameters in a smallest direction e.g. smooth muscle cells and endothelial cells will require substantial porosity of the substrate, but will have to provide pores small enough to support the cell. Given this constraint, it is desirable to have less than 20%, more preferably less than 15% and more preferably less than 10% of the fiber diameters above 20 μm, and at least 40%, more preferably at least 45% of the fiber diameters below 10 μm. The porosity shown in FIG. 8 demonstrate that all of examples B, C and E (i.e. M2, M3, and M5) have substantially this distribution, which is believed to account for the remarkable adhesion and growth of these cells on these mats demonstrated below.

Furthermore, as is known in the art, successful grafts integrate with the existing blood vessels. Blood vessels have luminal cellular layer formed by endothelial cells (EC), and consequently it is desired to provide grafts that permit continuity of the luminal layer. Likewise an abluminal layer of the blood vessels are formed with smooth muscle cells (SMC), and it is desirable to provide grafts that will permit continuity of the abluminal layer. Preferably the luminal and abluminal layers are formed with like cells to effectively provide continuation of the blood vessel, for many functions including vasodilatation.

The surface pore size distributions of mats M1 . . . M5 look promising for the ingrowth of ECs and SMCs which would permit a graft formed of this non-woven fiber mat to retain and nourish ECs and SMCs. This could be performed by providing a temporary or permanent seal for the graft until the EC and SMC ingrowth is complete after implantation, but preferably the graft is seeded with ECs and/or SMCs prior to implantation.

Accordingly the mats prepared as described above were studied for their response to culture of endothelial cells (EC) and smooth muscle cells (SMC). Fiber diameter distribution and pore size distribution are thought to have an effect on cell attachment and growth.

It is known in the art to functionalize grafts by applying compounds to improve the adherence of cells and their proliferation. One of the most common compounds used is gelatin. Accordingly, the tests for cellular attachment below are repeated with and without pretreatment of gelatin.

Cell Culture

Human brain endothelial cells (HBEC) were obtained from small intracortical microvessels and capillary fractions (20-112 μm) harvested from human temporal cortex excised surgically from patients treated for idiopathic epilepsy. Tissues were obtained with approval from the Institutional Research Ethics Committee. HBEC were separated from smooth muscle cells with cloning rings and grown in media containing Earle's salts, 25 mM 4-(2-hydroxyethyl)-1-piperazineethanesulfonic acid (HEPES), 4.35 g/L sodium bicarbonate, and 3 mM L-glutamine, 10% FBS, 5% human serum, 20% of media conditioned by murine melanoma cells (mouse melanoma, Cloudman S91, clone M-3, melanin-producing cells), 5 μg/ml insulin, 5 μg/ml transferrin, 5 ng/ml selenium, and 10 mg/ml endothelial cell growth supplement (Stanimirovic et al., 1996). Cells were grown at 37° C. in humidified atmosphere of 5% $CO_2$/95% air until about 80% confluence was reached. HBEC cultures were routinely characterized morphologically and biochemically. More than 95% of cells in culture: 1-stained immunopositive for the selective endothelial markers: angiotensin II-converting enzyme and Factor VIII-related antigen; 2-incorporated fluorescently labelled Ac-LDL; and 3-exhibited high activities of the blood-brain barrier-specific enzymes: γ-glutamyl-transpeptidase and alkaline phosphatase (Stanimirovic et al. (1996) *J Cell Physiol* 169: 455-467).

Human aortic smooth muscle cells (AoSMC) were obtained from Clonetics (Walkersville, Md., USA) and cultured in smooth muscle growth media (SmGM®-2 Bullet-Kit®, Clonetics) at 37° C. in humidified atmosphere of 5% $CO_2$/95% air until reach about 80% confluence. More than 95% of the AoSMC in cultures stained immunopositive for the selective smooth muscle marker α-actin.

HBEC and AoSMC were respectively trypsinized with 1 ml of either GRP-2 (Cells systems) or GIBCO (0.25%) trypsin. The mats M1 . . . M5 were punched into discs, and the discs were placed on Falcon 24-well plates and pre-wetted overnight either with cell media or with 0.5% gelatin. 50 μl of culture media containing $10^5$ cells were applied to the meshes and let sit for 20 min before filling the wells with additional 450 μl of media. Cells were allowed to grow on the meshes for 6 days at 37° C. in humidified atmosphere of 5% $CO_2$/95% air.

HBEC and AoSMC Staining

To visualize and quantify the number of living cells on the mats (planar discoidal scaffolds), cells were washed twice with warm Hank's balanced saline solution (HBSS), incubated with 10 µg/ml a vital dye called CFDA™ (Molecular Probes, Invitrogen Corp.) at 37° for 45 minutes and then washed again with HBSS. Fluorescence of the cells grown both on the meshes and on the bottom of the well (after removing the meshes) was measured using a cytofluorimeter plate reader (Bio-Tex FL600) at 485 nm ex/530 nm em.;

HBEC and AoSMC grown on uncoated scaffolds were fixed with 4% paraformaldehide for 10 min at room temperature (RT). Cells were then rinsed 4 times with HBSS, and permeabilized with 0.1% Triton™ X-100 (EM Science Gibbstown, N.J., USA) in HBSS at RT for 10 min. After rinsing, cells were blocked with 4% serum in HBSS for 1 h at RT. HBEC were then incubated with mouse anti collagen IV primary antibody (1:500 dilution, Abcam, Cambridge, Mass., USA) while AoSMC were incubated with mouse anti-smooth muscle α-actin primary antibody (1:500 dilution, R&D systems, Minneapolis, Minn., USA) and rabbit anti-elastin primary antibody (1:500, Ciderlan, Hornby, ON, Canada) for 1 h at RT. Cells were rinsed twice with HBSS, and HBEC were exposed to both goat-antimouse Alexa™ Fluor 568 secondary antibody (1:500 dilution, Molecular Probes, Burlington, ON, Canada) and Fluorescein *Ulex Europaeus* Agglutinin-1 (Vector Lab. Inc., Birlingame, Calif., USA) while AoSMC were exposed to goat anti-rabbit Alexa Fluor 488 secondary antibody (1:500 dilution, Molecular Probes) and goat anti-mouse Alexa Fluor 568 secondary antibody (1:500 dilution) for 30 min at RT. Cells were rinsed twice with HBSS and covered with DAKO mounting media spiked with DAPI (2 µg/ml, Sigma Aldrich, Oakville, ON, Canada) and placed on glass slides.

Microphotographs of the cells attached to the mats were taken using an Olympus 1×50 microscope. Images were captured using a digital video camera (Olympus U-CMT) and analyzed with Northen Eclipse v.5.0 software.

Figure 10:
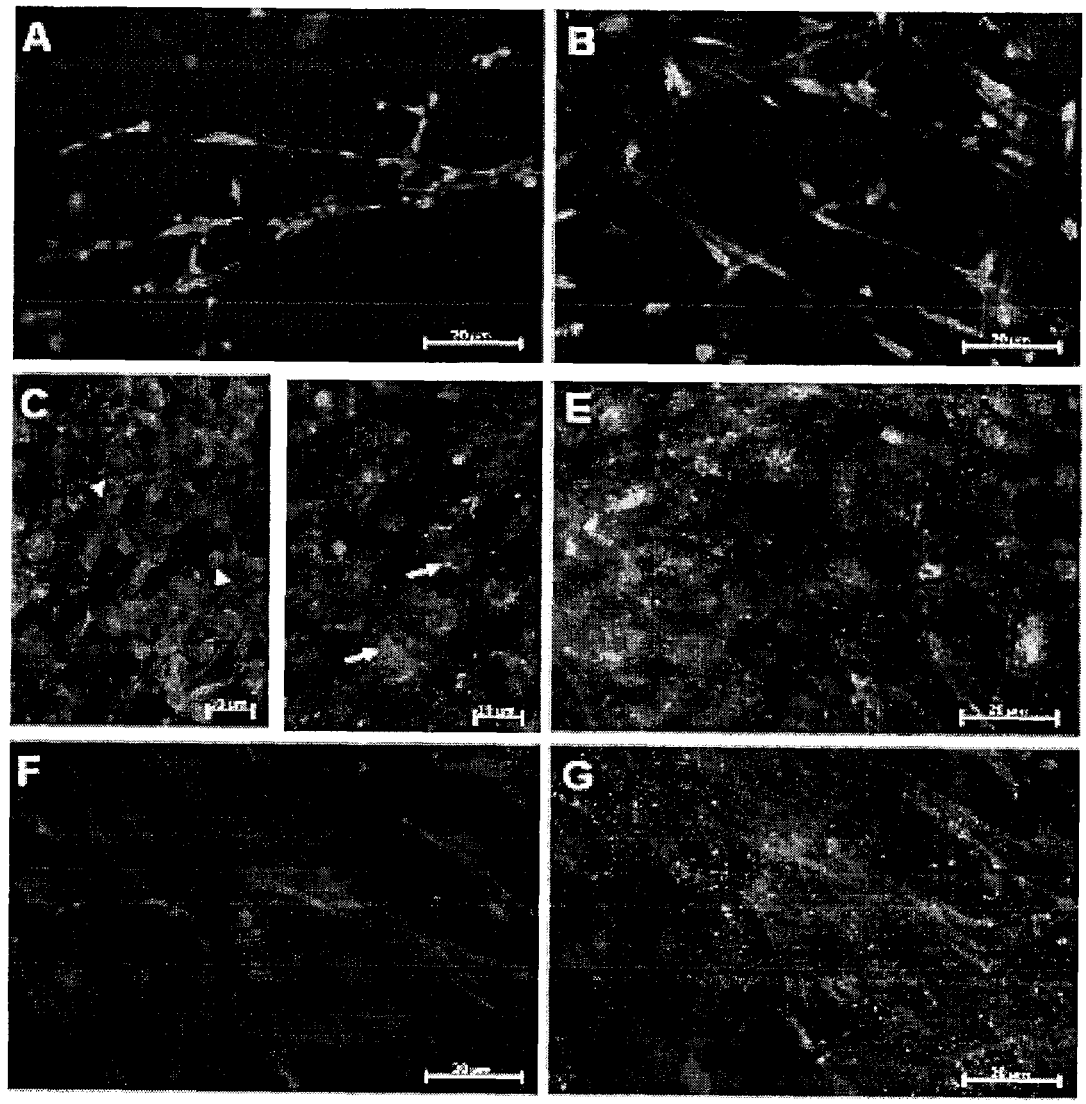
FIGS. 10A,B,C,D,E,F and G are photo-micrographs of HBEC (A, C, D and E) and AoSMC (B, E, F and G) growing on mat M5, the mat serving as scaffold for the cells. HBEC (A) and AoSMC (B), stained with the vital dye CFDA-AM, attached to the nonwoven mats with the body elongated following the direction of the fibers. HBEC labeled with fluorescein-conjugated UEA-1 (green) (C) showed marked staining surrounding the plasma membrane (head arrow). HBEC immunofluorescently labeled with antibodies against Factor VIII related-antigen (D) showed intracellular granular staining (arrow). HBEC stained with fluorescein-conjugated UEA-1 (green) and antibodies against type IV collagen (red) (E). Immunostaining of AoSMC with antibodies against anti-smooth muscle α-actin (red) (F-G) and anti-elastin antibodies (green). Cellular nuclei were stained with DAPI (blue) (C-G)

HBEC (FIG. 10A) and AoSMC (FIG. 10B) stained with the vital dye CFDA-AM showed attachment to the mats. The cells were elongated and aligned following the direction of the fibers (FIG. 10A-B). After 6 days, the mat appeared completely populated with cells that spread through the polymer (FIGS. 10C-E) and retained their specific molecular markers; HBEC expressed factor VIII (FIG. 10C) and bound *Ulex Europaeus* I lectin (FIGS. 9D-E) and AoSMC expressed α-actin (FIGS. 9F-G). In addition, HBEC expressed collagen IV (FIG. 9E), an ECM that provides stiffness to the vascular wall and AoSMC expressed elastin (FIG. 9G), an ECM responsible for elastic recoil of arteries.

The fact that some control over a degree of fiber orientation is provided by controlling a roller speed and position relative to the other parameters of the extrusion fiber blow melt web formation, presents the possibility of allowing the design of the mats with optimal web orientation to minimize risks of thrombogenicity. For example luminal webs oriented with the fibers aligned in the direction of the vascular long axis and to maximize smooth muscle contractibility abluminal webs may be orientated with the fibers aligned circumferentially in the direction of the short axis.

Because the mats are composed of fibers, there are networks of porosities running through them. The network-porosity of these mats suggest that communications paths and fluid channels would be provided between ECs and SMCs in a similar manner to how they are provide by the matrix of elastin and collagen fibers that form the media, and consequently will facilitate integration of the graft within these walls.

Both HBEC and AoSMC preserved their specific cellular phenotype when seeded on mat M5 (i.e. structure E). HBEC retained both the expression of Factor VIII-related antigen [Hormia et al. (1983) *Experimental Cell Research* 149(2): 483-497.], a classic marker of endothelium that forms complexes with Von Willebrand factor (vWF), and the binding capacity to *Ulex Europaeus* I agglutinin, a lectin that selectively recognizes L-fucose moieties of multiple glycoproteins present on the surface of endothelial cells [Hormia et al. (1983) *Experimental Cell Research* 149(2):483-497; Holthofer et al. (1982) *Laboratory Investigation; A Journal of Technical Methods and Pathology* 47(1):60-66]. AoSMC also maintained their capacity to express smooth muscle alpha actin, a selective marker of vascular SMC that has been shown to be regulated by hormones, cell proliferation, and altered by pathological conditions including oncogenic transformation and atherosclerosis [Chaponnier and Gabbiani (2004) *The Journal of Pathology* 204(4):386-395].

The elastic properties of large arteries and their capacity to synthesize vasoactive substances are key elements for the ability of the arterial wall to function as a modulator of blood pressure and cardiovascular hemodynamics. The passive biomechanical properties of the arterial wall are influenced predominantly by the extra-cellular matrix (ECM) proteins, collagen and elastin. Collagen provides the tensile stiffness for the resistance against rupture while elastin dictates the elastic properties of the blood vessels. Combined with collagen, elastin prevents irreversible deformation of the vessel against pulsatile flow [Faury (2001) *Pathologie-biologie* 49(4):310-325]. Alterations in collagen and elastin vascular content have been associated to pathological conditions such as artery stiffening and resistance artery narrowing, two key features that contribute to the development of hypertension [Arribas et al. (2006) *Pharmacology & Therapeutics* 111(3):771-791]. HBEC and AoSMC growing on the mats expressed collagen and elastin, respectively, indicating that the cells not only preserve their phenotype but they also retain their capacity to produce ECM proteins essential to maintain EC-SMC communication and modulate vascular cellular functions such as cell proliferation, adhesion and migration [Brooke et al. (2003) *Trends in Cell Biology* 13(1):51-56].

Figure 11:
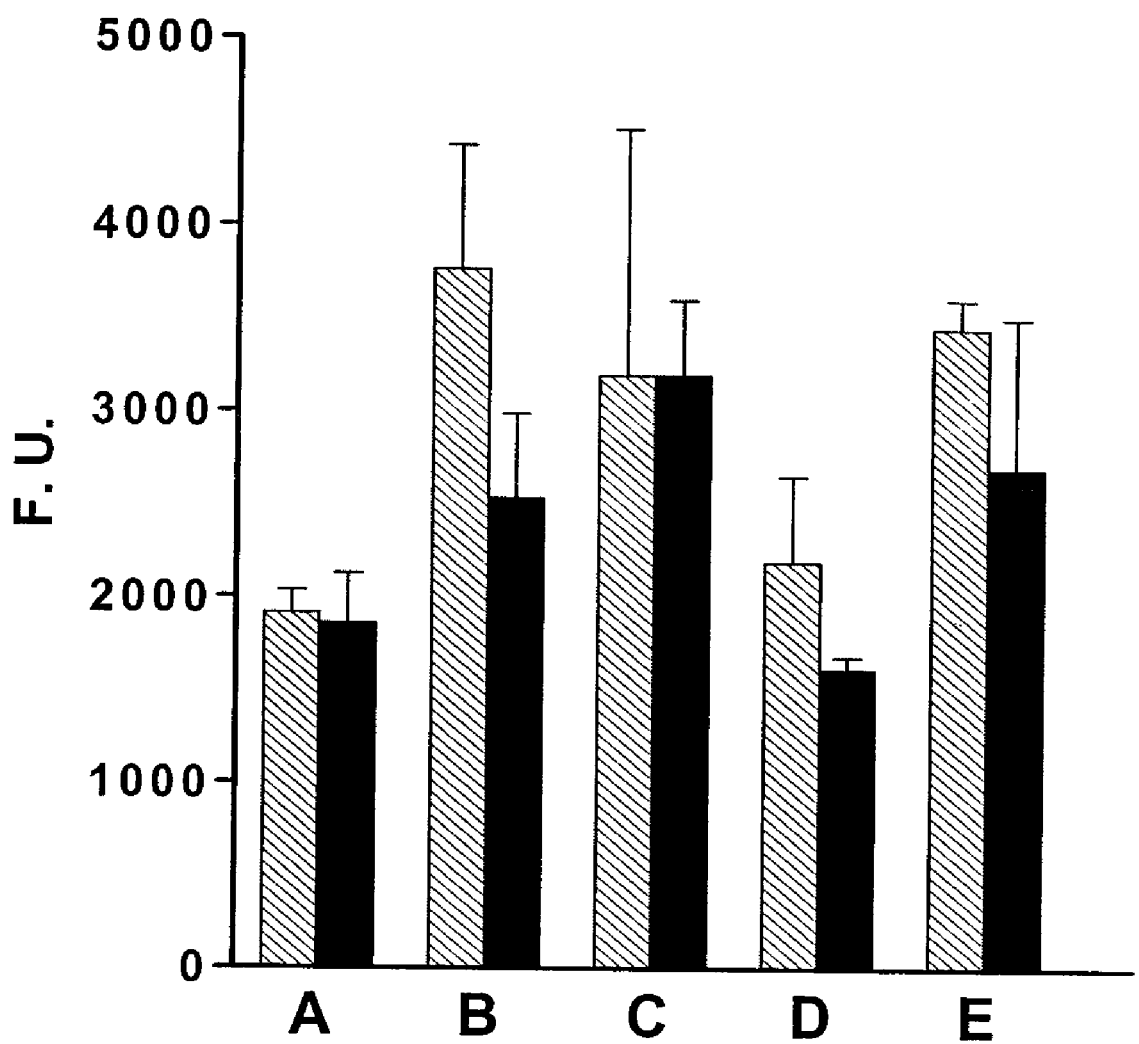
FIG. 11 is a chart showing mean of fluorescent units of vital staining with CFDA-SE of HBEC grown for 6 days on uncoated (hatched bars) or gelatin-coated (solid bars) mats M1 . . . M5.
Figure 12:
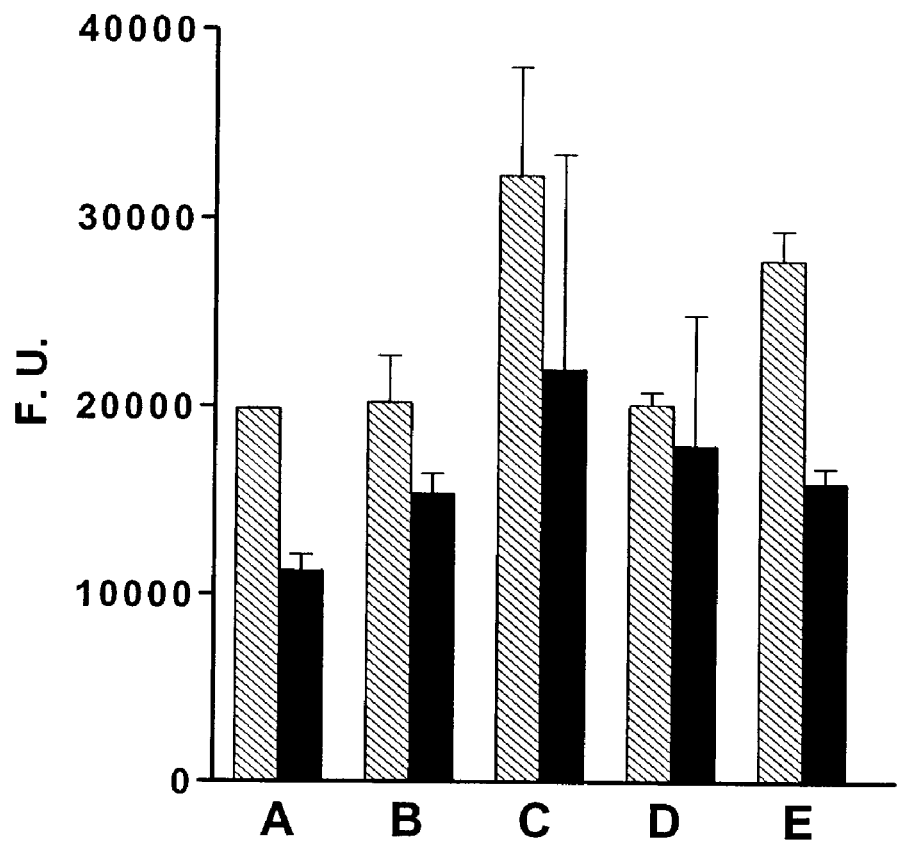
FIG. 12 is a chart showing mean of fluorescent units of vital staining of AoSMC grown for 6 days on uncoated (hatched bars) or gelatin-coated (solid bars) mats M1 . . . M5.

FIGS. 11 and 12 are charts showing fluorescence emitted by the cells stained with the vital dye CFDA-AM. Bars represent fluorescence units of light emitted at 530 nm under excitation at 485 nm. The uncertainty was derived from standard deviations of 2 experiments performed in triplicate. FIG. 11 represents HBEC cell populations, whereas FIG. 12 represents AoSMC populations on M1 . . . M5. The solid bars refer to samples that were presoaked in gelatin, and the cross-hatched bars refer to non-pretreated mats (soaked only in cell culture). Surprisingly the M1 . . . M5 were better designed to hold the cells without the assistance of gelatin.

cAMP Production

As is also known, calcitonin gene related peptide (CGRP) is one of the most potent vasodilators. Its vascular effect is mediated by activation of adenylate cyclase and the subsequent formation of cAMP in smooth muscle and endothelial cells. Accordingly cAMP production is a measure of the ability of the EC seeded on the mats to respond to vasodilator agents such as CGRP.

The effect of CGRP in the production of cAMP was assessed in HBEC growing on mat M5. The cells were incubated (10 min) with increasing concentrations (0.5-1 µM) of CGRP in phosphate buffer saline containing 0.2% bovine serum albumin and 1 mM 3-isobutyl-1-methyl-xanthine. Levels of cAMP were determined with a commercial enzyme immunoassay kit (Biotrak, Amersham). The cells were dissolved in 0.1 NaOH and protein content measured by Lowry's method. cAMP levels were expressed as a function of protein content in cell extracts.

Figure 13:
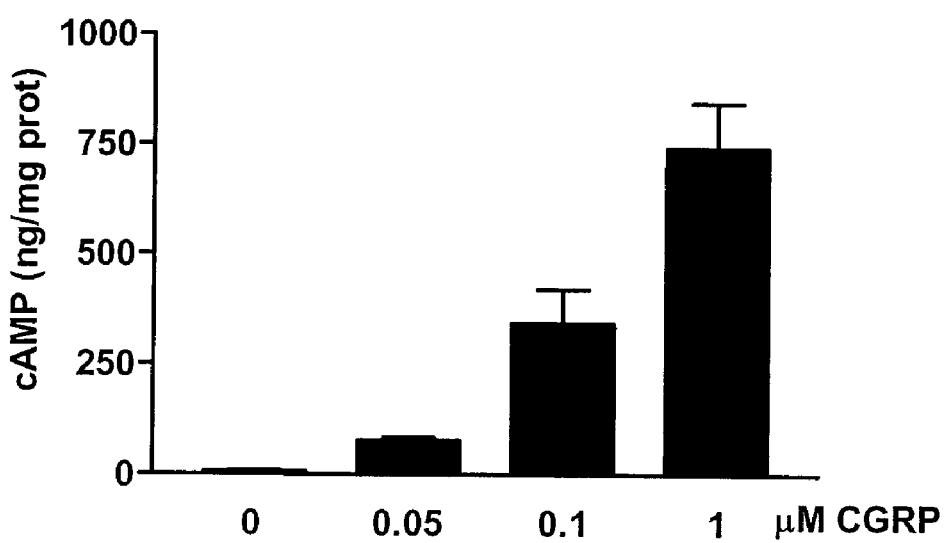
FIG. 13 is a chart showing cAMP formation in response to different concentrations of CGRP by HBEC grown in mat M5.

The results shown in FIG. 13 indicate an increase in cAMP production in response to increasing concentrations of CGRP.

The active biomechanical properties of the arterial wall depend on the activation of vascular SMC either directly or through endothelial cell-dependent mechanisms. CGRP is a potent dilator of human brain arteries [Moreno et al. (2002) *Neuropharmacology* 42(4):568-576], ~100 to 1000 times more potent than other vasodilators such as adenosine, SP, or acetylcholine. It acts through activation of type II G-protein-coupled receptors located in both EC and SMC and posterior stimulation of adenylate cyclase activity [Moreno et al. (2004) *Encyclopedia of Endocrinology and Endocrine Diseases* (Academic Press. Elsevier Inc.) 1:421-435]. Reduction of CGRP release from nerve terminals and down-regulation of CGRP receptor expression in vascular tissues have been reported to be involved in the pathophysiology of hypertension [Deng and Li (2005) *Peptides* 26(9):1676-1685]. EC seeded on mat M5 responded to CGRP producing similar levels of cAMP than those produced by EC seeded on gelatin-coated plastic discs. This indicates that the interaction of EC with the scaffolds neither alters the CGRP receptor expression nor the dilatory capacity mediated by cAMP formation of the EC.

In summary, in this study, nonwoven PET fiber mats were developed using a melt blown process, which were used as vascular scaffolds. This fabrication method allowed the control of fiber diameter, structural porosity and mechanical compliance. Following an iterative manufacturing/cell culture evaluation process, mats were obtained having porosity and fiber diameters required to produce good scaffolds. Both HBEC and AoSMC were able to proliferate and spread in the scaffolds, retained their characteristic cell phenotype (HBEC: factor VIII expression and *Ulex Europaeus* I lectin binding; AoSMC: α-actin expression) and respectively produced collagen and elastin. HBEC also preserved the ability to produce cAMP when stimulated with CGRP, a very potent vasodilator agent. Mechanical testing of the cylindrical mats showed compliance and deformation ranges similar to native artery values. In contrast, commercial woven or knitted PET fiber or ePTFE grafts have a 10-fold lower compliance. All together this indicates that the biomechanical and biocompatible characteristics of this novel scaffold are applicable as vascular grafts.

In conclusion, the mats M2, M3 and M5 present promising characteristics for vascular graft fabrication such as: controllable porosity, fiber orientation and compliance; no toxicity; good HBEC and AoSMC cell attachment and proliferation following fiber alignment; the retention of AC machinery for vasodilation of HBEC grown thereon; the comparability of elastic moduli of the mats with that of native arteries (~1 MPa), especially in comparison with those of Dacron or PTFE; and finally the low cost of manufacture.

Other advantages that are inherent to the mats are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A method of producing a mat comprising:
producing a web having a tangle of oriented parallel polymer strands contact fused at tangle points thereby defining an orientation of the web, wherein the strands have a diameter distribution such that at least the smallest 80% of strands have a mean strand diameter between 2 and 4.5 µm with a standard deviation within 2 µm and strand diameters are unimodal with a regression coefficient measure of fit to a normal distribution of at least 0.96;
laying 15 to 50 sections of the web in a stack so that the orientations of at least two web sections differ by an angle between 3° and 90°; and
applying heat and pressure to the stack of webs to produce a mat, the heat being at a temperature above a glass transition temperature and below a melting point of the polymer.

2. The method of claim 1 wherein stacking the webs comprises applying a group of one or more like orientation web sections above and below differently oriented web sections.

3. The method of claim 1 wherein stacking the webs comprises applying the webs onto a mold.

4. The method of claim 1 wherein producing a web comprises extruding and stretching the strands of a polycondensation polymer.

5. The method of claim 4 wherein the polycondensation polymer comprises one of: polyethylene terephthalate (PET), polycarbonate (PC), polytrimethylene terephthalate (PTT), and polylactic acid (PLLA), or a combination thereof.

6. The method of claim 1 wherein producing the plurality of webs comprises extrusion fiber melt blowing one or more webs and cutting the webs to form the plurality of web sections before, after, or during the laying of the web sections.

7. The method of claim 6 wherein the extrusion fiber melt blowing comprises subjecting a molten tangled strand output to a roller for providing a desired degree of orientation of the molten tangled strands.

8. The method of claim 5 wherein producing the web comprises applying selected parameters of an extrusion fiber blow melt process to provide PET strands having at least 80% of the diameters ranging over less than 4.5 µm.

9. The method of claim 1 wherein producing the web comprises applying selected parameters of an extrusion fiber blow melt process to provide PET strands in a web having a density of about 1.9 g/m².

10. A mat formed from 15 to 50 web sections of a same web stacked and compressed together, wherein:
the web is formed of oriented, extruded polymer strands contact-fused at tangle points, the strands in a given web section being parallel to one another thereby defining an orientation of the given web section, the orientations of at least two web sections differing by an angle between 3° and 90°; and
at least the smallest 80% of strands have a mean strand diameter between 2 and 4.5 µm with a standard deviation within 2 µm and strand diameters are unimodal with a regression coefficient measure of fit to a normal distribution of at least 0.96.

11. The mat of claim 10 wherein the web is produced by extrusion fiber melt blowing.

12. The mat of claim 10 wherein the polymer comprises a polycondensation polymer.

13. The mat of claim 12 wherein the polycondensation polymer is one of: polyethylene terephthalate (PET), polycarbonate (PC), polytrimethylene terephthalate (PTT), and polylactic acid (PLLA), or a combination thereof.

14. The mat of claim 10 wherein the polycondensation polymer is a polyester, and the orientations of the at least two web sections are orthogonal.

15. The mat of claim 10 wherein the web is produced of PET strands and has a porosity network with about 90% of the pores having a dimension less than 20 μm.

16. The mat of claim 15 wherein at least 50% of the pores have a mean diameter between 5 and 17 μm.

17. The mat of claim 14 wherein the mat is formed as a cylinder.

18. The mat of claim 10 wherein the mat is formed of a hollow cylinder having an average compliance between $7.4 \times 10^{-2}$%/mmHg and $9.4 \times 10^{-2}$%/mmHg.

* * * * *